United States Patent [19]
Li et al.

[11] Patent Number: 6,019,980
[45] Date of Patent: Feb. 1, 2000

[54] NUCLEIC ACID RESPIRATORY SYNCYTIAL VIRUS VACCINES

[75] Inventors: Xiaomao Li, Thornhill; Mary E. Ewashysyn; Michel H. Klein, both of Willowdale, all of Canada

[73] Assignee: Connaught Laboratories Limited, Willowdale, Canada

[21] Appl. No.: 08/476,397

[22] Filed: Jun. 7, 1995

[51] Int. Cl.[7] .............................. C12N 15/63; A61K 31/70
[52] U.S. Cl. ..................... 424/211.1; 435/320.1; 514/44
[58] Field of Search .................. 435/69.1, 69.3, 435/320.1; 536/23.1, 23.72, 24.1; 514/44; 424/211.1

[56] References Cited

U.S. PATENT DOCUMENTS 5,149,650  9/1992  Wertz et al. ............................ 435/243

FOREIGN PATENT DOCUMENTS

WO 93/21310  10/1993  WIPO .

OTHER PUBLICATIONS

Chanock, Robert M. et al, Pediatrics vol. 90 No. 1, Jul. 1992, pp. 137–142.
Prince et al, J. Virol., 61:1851–1854, Jun. 1987.
Crowe et al, PNAS 91:1386–1390, Feb. 1994.
Prince et al, J. Virol. 55:517; Virus Res. 3; 193–206, 1985.
Groothuis et al, N. Engl. J. Med. 329:1524–1530, Nov. 1993.
Walsh et al, J. Infec. Dis., 155: 1198–1204, Jun. 1987.
Paradiso et al, Pediatr. Infect. Dis. J. 13:792–798, 1994.
Hemming et al, J. Infect. Dis., 152:1083–1087, (1985).
Tang et al. (1993) J. Biol. Chem. 268:9522–9525.
Collis et al. (1990) EMBO J. 9:233–240.

*Primary Examiner*—David Guzo
*Assistant Examiner*—Robert Schwartzman
*Attorney, Agent, or Firm*—Sim & McBurney

[57] ABSTRACT

Vectors containing a nucleotide sequence coding for an F protein of respiratory syncytial virus (RSV) and a promoter for such sequence, preferably a cytomegalovirus promoter, are described. Such vectors also may contain a further nucleotide sequence located adjacent to the RSV F protein encoding sequence to enhance the immunoprotective ability of the RSV F protein when expressed in vivo. Such vectors may be used to immunize a host, including a human host, by administration thereto. Such vectors also may be used to produce antibodies for detection of RSV infection in a sample.

10 Claims, 27 Drawing Sheets

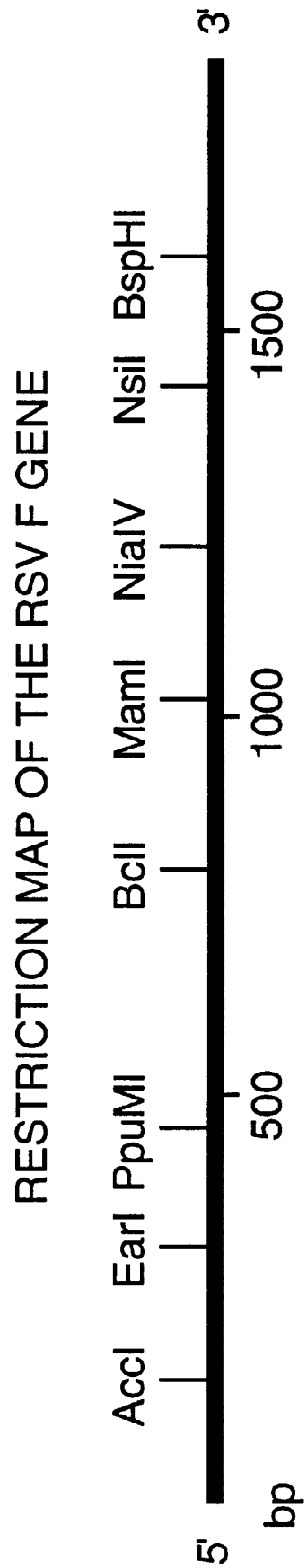

NUCLEOTIDE SEQUENCE OF THE RSV F GENE.

SP

5' MET GLU LEU PRO ILE LEU LYS ALA ASN ALA ILE THR THR ILE LEU ALA ALA VAL THR PHE
ATGGAGTTGCCAATCCTCAAAGCAAATGCAATTACCACAATCCTCGCTGCAGTCACATTT
TACCTCAACGGTTAGGAGTTTCGTTTACGTTAATGGTGTTAGGAGCGACGTCAGTGTAAA
10 20 30 40 50 60

CYS PHE ALA SER SER GLN ASN ILE THR GLU GLU PHE TYR GLN SER THR CYS SER ALA VAL
TGCTTTGCTTCTAGTCAAAACATCACTGAAGAATTTTATCAATCAACATGCAGTGCAGTT
ACGAAACGAAGATCAGTTTTGTAGTGACTTCTTAAAATAGTTAGTTGTACGTCACGTCAA
70 80 90 100 110 120

SER LYS GLY TYR LEU SER ALA LEU ARG THR GLY TRP TYR THR SER VAL ILE THR ILE GLU
AGCAAAGGCTATCTTAGTGCTCTAAGAACTGGTTGGTATACTAGTGTTATAACTATAGAA
TCGTTTCCGATAGAATCACGAGATTCTTGACCAACCATATGATCACAATATTGATATCTT
130 140 150 160 170 180

LEU SER ASN ILE LYS GLU ASN LYS CYS ASN GLY THR ASP ALA LYS VAL LYS LEU MET LYS
TTAAGTAATATCAAGGAAAATAAGTGTAATGGAACAGATGCTAAGGTAAAATTGATGAAA
AATTCATTATAGTTCCTTTTATTCACATTACCTTGTCTACGATTCCATTTTAACTACTTT
190 200 210 220 230 240

GLN GLU LEU ASP LYS TYR LYS ASN ALA VAL THR GLU LEU GLN LEU LEU MET GLN SER THR
CAAGAATTAGATAAATATAAAAATGCTGTAACAGAATTGCAGTTGCTCATGCAAAGCACA
GTTCTTAATCTATTTATATTTTTACGACATTGTCTTAACGTCAACGAGTACGTTTCGTGT
250 260 270 280 290 300

PRO ALA ALA ASN ASN ARG ALA ARG ARG GLU LEU PRO ARG PHE MET ASN TYR THR LEU ASN
CCAGCAGCAAACAATCGAGCCAGAAGAGAACTACCAAGGTTTATGAATTATACACTCAAC
GGTCGTCGTTTGTTAGCTCGGTCTTCTCTTGATGGTTCCAAATACTTAATATGTGAGTTG
310 320 330 340 350 360

FIG.2B.

```
                                                                    F2-F1CLEAVAGE SITE
ASN THR LYS LYS THR ASN VAL THR LEU SER LYS LYS ARG LYS ARG ARG▼PHE LEU GLY PHE
AATACCAAAAAACCAATGTAACATTGTAATTCGTTCTTTCCTTTCTTAAGAAGATTCTTGGTTTT
TTATGGTTTTTTGGTTACATTGTAACATTAAGCAAGAAAAGGAAAA8AAGATTCTTAAAGAACCAAAA
         370         380         390         400         410         420
LEU LEU GLY VAL GLY SER ALA ILE ALA SER GLY ILE ALA VAL SER LYS VAL LEU HIS LEU
TTGTTAGGTGTTGGATCTGCAATCGCCAGTGGCATTGCTGTATCTAAGGTCCTGCACTTA
AACAATCCACAACCTAGACGTTAGCGGTCACCGTAACGACATAGATTCCAGGACGTGAAT
         430         440         450         460         470         480
GLU GLY GLU VAL ASN LYS ILE LYS SER ALA LEU LEU SER THR ASN LYS ALA VAL VAL SER
GAAGGAGAAGTGAACAAGATCAAAAGTGCTCTACTATCCACAAACAAGGCCGTAGTCAGC
CTTCCTCTTCACTTGTTCTAGTTTTCACGAGATGATAGGTGTTGTTCCGGCATCAGTCG
         490         500         510         520         530         540
LEU SER ASN GLY VAL LEU THR SER LYS VAL LEU ASP LEU LYS ASN TYR ILE ASP
TTATCAAATGGAGTTAGTGTCTTAACCAGCAAAGTGTTAGACCTCAAAAACTATATAGAT
AATAGTTTACCTCAATCACAGAATTGGTCGTTTCACAATCTGGAGTTTTGATATATCTA
         550         560         570         580         590         600
LYS GLN LEU LEU PRO ILE VAL ASN LYS GLN SER CYS ARG ILE SER ASN ILE GLU THR VAL
AAACAATTGTTACCTATTGTGAATAAGCAAAGCTGCAGAATATCAAATAAAACTGTG
TTTGTTAACAATGGATAACACTTATTCGTTTCGACGTCTTATAGTTTATATCTTTGACAC
         610         620         630         640         650         660
ILE GLU PHE GLN HIS LYS ASN ASN ARG LEU LEU GLU ILE THR ARG GLU PHE SER VAL ASN
ATAGAGTTCCAACAAAGAACAACAGAGACTACTAGAGATTACCAGGGAATTTAGTGTTAAT
TATCTCAAGGTTGTTTTCTTGTTGTCTCTGATGATCTCTAATGGTCCCTTAAATCACAATTA
         670         680         690         700         710         720
ALA GLY VAL THR THR PRO VAL SER THR TYR MET LEU THR ASN SER GLU LEU LEU SER LEU
GCAGGTGTAACTACACCTGTAAGCACTTACATGTTAACTAATAGTGAATTATTGTCATTA
CGTCCACATTGATGTGGACATTCGTGAATGTACAATTGATTATCACTTAATAACAGTAAT
         730         740         750         760         770         780
```

FIG.2C.

```
ILE ASN ASP MET PRO ILE THR ASN ASP GLN LYS LYS LEU MET SER ASN ASN VAL GLN ILE
ATCAATGATATGCCTATAACAAATGATCAGAAAAAGTTAATGTCCAACAATGTCAAATA
TAGTTACTATACGGATATTGTTTACTAGTCTTTTCAATTACAGGTTGTTACAAGTTTAT
         790           800           810           820           830           840

VAL ARG GLN GLN SER TYR SER ILE MET SER ILE ILE LYS GLU GLU VAL LEU ALA TYR VAL
GTTAGACAGCAAAGTTACTCTATCATGTCCATAATAAAAGAGGAAGTCTTAGCATATGTA
CAATCTGTCGTTCAATGAGATAGTACAGGTATTATTTTCTCCTTCAGAATCGTATACAT
         850           860           870           880           890           900

VAL GLN LEU PRO LEU TYR GLY VAL ILE ASP THR PRO CYS TRP LYS LEU HIS THR SER PRO
GTACAATTACCACTATATGGTGTGATAGATACACCTGTTGGAAATTACACACATCCCT
CATGTTAATGGTGATATACCACACTATCTATGTGGAACAACCTTTAATGTGTGTAGGGA
         910           920           930           940           950           960

LEU CYS THR THR ASN THR LYS GLU GLY SER ASN ILE CYS LEU THR ARG THR ASP ARG GLY
CTATGTACAACCAACAAACACAAAAGAAGGGTCAAACATCTGTTTAACAAGAACTGACAGAGA
GATACATGTTGGTTGTTGTTTCTTCCCAGTTTGTAGACAAATTGTTCTTGACTGTCTCCT
         970           980           990          1000          1010          1020

TRP TYR CYS ASP ASN ALA GLY SER VAL SER PHE PHE PRO GLN ALA GLU THR CYS LYS VAL
TGGTACTGTGACAATGCAGGATCAGTATCTTTCTTCCCACAAGCTGAAACATGTAAAGTT
ACCATGACACTGTTACGTCCTAGTCATAGAAAGAAGGGTGTTCGACTTTGTACATTCAA
        1030          1040          1050          1060          1070          1080

GLN SER ASN ARG VAL PHE CYS ASP THR MET ASN SER LEU THR LEU PRO SER GLU VAL ASN
CAATCGAATCGAGTATTTGTGACACAATGAACAGTTTAACATTACCAAGTGAAGTAAAT
GTTAGCTTAGCTCATAAAACACTGTGTTACTTGTCAAATTGTAATGGTTCACTTCATTTA
        1090          1100          1110          1120          1130          1140

LEU CYS ASN VAL ASP ILE PHE ASN PRO LYS TYR ASP CYS LYS ILE MET THR SER LYS THR
CTCTGCAATGTTGACATATTCAATCCCAAATATGATTGTAAAATTATGACTTCAAAACA
GAGACGTTACAACTGTATAAGTTAGGGTTTATACTAACATTTTAATACTGAAGTTTTGT
        1150          1160          1170          1180          1190          1200
```

FIG.2D.

```
ASP VAL SER SER SER VAL ILE THR SER LEU GLY ALA ILE VAL SER CYS TYR GLY LYS THR
GATGTAAGCAGCAGCTCCGTTATCACATCTCTAGGAGCCATTGTGTCATGCTATGGCAAAACT
CTACATTCGTCGTCGAGGCAATAGTGTAGAGATCCTCGGTAACACAGTACGATACCGTTTTGA
     1210              1220              1230              1240              1250              1260

LYS CYS THR ALA SER ASN LYS ASN ARG GLY ILE ILE LYS THR PHE SER ASN GLY CYS ASP
AAATGTACAGCATCCAATAAAAATCGTGGAATCATAAAGACATTTTCTAACGGGTGTGAT
TTTACATGTCGTAGGTTATTTTTAGCACCTTAGTATTTCTGTAAAAGATTGCCCACACTA
     1270              1280              1290              1300              1310              1320

TYR VAL SER ASN LYS GLY [VAL] ASP THR VAL SER VAL GLY ASN THR LEU TYR TYR VAL ASN
TATGTATCAAATAAAGGGTGTGACACTGTCTCTAGGTAACACATTATATTATGTAAAT
ATACATAGTTTATTTCCCCACACTGTGACAGAGATCCATTGTGTAATAATACATTTA
     1330              1340              1350              1360              1370              1380

LYS GLN GLY LYS SER LEU TYR VAL LYS GLY GLU PRO ILE ILE ASN PHE TYR ASP PRO
AAGCAAGAAGGCAAAAGTCTCTATGTAAAAGGTGAACCAATAATAAATTTCTATGACCCA
TTCGTTCTTCCGTTTTCAGAGATACATTTTCCACTTGGTTATTATTTAAAGATACTGGGT
     1390              1400              1410              1420              1430              1440

LEU VAL PHE PRO SER ASP ALA SER ILE SER GLN VAL ASN GLU LYS ILE ASN
TTAGTATTTCCCCCTCTGATGCATCAATCTCAAGTCAATGAGAAGATTAAC
AATCATAAGGGGAGACTACTTAAAAATAAGCATTAGGCTACTTACATGTAAATGCTACGACCATTG
     1450              1460              1470              1480              1490              1500

GLN SER LEU ALA PHE ILE ARG LYS SER ASP GLU LEU LEU HIS ASN VAL ASN ALA GLY LYS
CAGAGTTTAGCATTTATTCGTAAATCCGATGAATTATTACATAATGTAAATGCTGGTAAA
GTCTCAAATCGTAAATAAGCATTTAGGCTACTTAATAATGTATTACATTTACGACCATTT
     1510              1520              1530              1540              1550              1560
                                            TM→
SER THR THR ASN ILE MET ILE THR THR ILE ILE ILE GLU ILE ILE LEU VAL ILE LEU LEU SER
TCAACCACAAATATCATGATAACTACTATAATTATAGAGATTATAGTAATATTGTTATCA
AGTTGGTGTTTATAGTACTATTGATGATATTGATGATATTAATATCTCTAATAATCATTATAACAATAGT
     1570              1580              1590              1600              1610              1620
```

```
LEU ILE ALA VAL GLY LEU LEU LEU TYR CYS LYS ALA ARG SER THR PRO VAL THR LEU SER
TTAATTGCTGTTGGACTGCTCCTATACTGTAAGGCCAGAAGCACACCAGTCACACTAAGC
AATTAACGACAACCTGACGAGGATATGACATTCCGGTCTTCGTGTGGTCAGTGTGATTCG
              1630              1640              1650              1660              1670              1680

LYS, ASP GLN LEU SER GLY ILE ASN ASN ILE ALA PHE SER ASN
AAGGATCAACTGAGTGGTATAAATAATATTGCATTTAGTAACTGAATAAAAATAGCACCT
TTCCTAGTTGACTCACCATATTTATTATAACGTAAATCATTGACTTATTTTATCGTGGA
              1690              1700              1710              1720              1730              1740

AATCATGTTCTTACAATGGTTTACTATCTGCTCATAGACAACCCATCTATCATTGGATTT
TTAGTACAAGAATGTTACCAAATGATAGACGAGTATCTGTTGGGTAGATAGTAACCTAAA
              1750              1760              1770              1780              1790              1800

TCTTAAAATCTGAACTTCATCGAAACTCTTATCTATAAACCATCTCACTTACACTATTTA
AGAATTTTAGACTTGAAGTAGCTTTGAGAATAGATATTTGGTAGAGTGAATGATGATAAAT
              1810              1820              1830              1840              1850              1860

AGTAGATTCCTAGTTTATAGTTTATAT 3'
TCATCTAAGGATCAAATATCAAATATA
              1870              1880
```

NUCLEOTIDE SEQUENCE OF THE RSV F GENE.

SP

5' MET GLU LEU PRO ILE LEU LYS ALA ASN ALA ILE THR THR ILE LEU ALA ALA VAL THR PHE
ATGGAGTTGCCAATCCTCAAAGCAAATGCAATTACCACAATCCTCGCTGCAGTCACATTT
TACCTCAACGGTTAGGAGTTTCGTTTACGTTAATGGTGTTAGGAGCGACGTCAGTGTAAA
10 20 30 40 50 60

CYS PHE ALA SER SER GLN ASN ILE THR GLU GLU PHE TYR GLN SER THR CYS SER ALA VAL
TGCTTTGCTTCTAGTCAAAACATCACTGAAGAATTTTATCAATCAACATGCAGTGCAGTT
ACGAAACGAAGATCAGTTTTGTAGTGACTTCTTAAAATAGTTAGTTGTACGTCACGTCAA
70 80 90 100 110 120

SER LYS GLY TYR LEU SER ALA LEU ARG THR GLY TRP TYR THR SER VAL ILE THR ILE GLU
AGCAAAGGCTATCTTAGTGCTCTAAGAACTGGTTGGTATACTAGTGTTATAACTATAGAA
TCGTTTCCGATAGAATCACGAGATTCTTGACCAACCATATGATCACAATATTGATATCTT
130 140 150 160 170 180

LEU SER ASN ILE LYS GLU ASN LYS CYS ASN GLY THR ASP ALA LYS VAL LYS LEU MET LYS
TTAAGTAATATCAAGGAAAATAAGTGTAATGGAACAGATGCTAAGGTAAAATTGATGAAA
AATTCATTATAGTTCCTTTTATTCACATTACCTTGTCTACGATTCCATTTTAACTACTTT
190 200 210 220 230 240

GLN GLU LEU ASP LYS TYR LYS ASN ALA VAL THR GLU LEU GLN LEU LEU MET GLN SER THR
CAAGAATTAGATAAATATAAAAATGCTGTAACAGAATTGCAGTTGCTCATGCAAAGCACA
GTTCTTAATCTATTTATATTTTTACGACATTGTCTTAACGTCAACGAGTACGTTTCGTGT
250 260 270 280 290 300

PRO ALA ALA ASN ASN ARG ALA ARG ARG GLU LEU PRO ARG PHE MET ASN TYR THR LEU ASN
CCAGCAGCAAACAATCGAGCCAGAAGAGAACTACCAAGGTTTATGAATTATACACTCAAC
GGTCGTCGTTTGTTAGCTCGGTCTTCTCTTGATGGTTCCAAATACTTAATATGTGAGTTG
310 320 330 340 350 360

FIG.3B.

```
                                                                                    F2-F1CLEAVAGE SITE
ASN THR LYS LYS THR ASN VAL THR LEU SER LYS LYS ARG LYS ARG ARG PHE LEU GLY PHE
AATACCAAAAAAACCAATGTAACATTAAGCAAGAAAAGAAAAAGAAAA8AAGATTTCTTGGTTTT
TTATGGTTTTTGTTACATTGTAATTCGTTCTTTCCTTTCTTTCTTTCTAAAGAACCAAAA
          370            380            390            400            410            420

LEU LEU GLY VAL GLY SER ALA ILE ALA SER GLY ILE ALA VAL SER LYS VAL LEU HIS LEU
TTGTTAGGTGTTGGATCTGCAATCGCCAGTGGCATTGCTGTATCTAAGTCCTGCACTTA
AACAATCCACAACCTAGACGTTAGCGGTCACCGTAACGACATAGATTCCAGGACGTGAAT
          430            440            450            460            470            480

GLU GLY VAL ASN LYS ILE LYS SER ALA LEU LEU SER THR ASN LYS ALA VAL VAL SER
GAAGGAGAAGTGAACAAGATCAAAAGTGCTCTACTATCCACAAACAAGCCGTAGTCAGC
CTTCCTCTTCACTTGTTCTAGTTTTCACGAGATGATAGGTGTTTGTTCCGGCATCAGTCG
          490            500            510            520            530            540

LEU SER ASN GLY VAL SER VAL LEU THR SER LYS VAL LEU ASP LEU LYS ASN TYR ILE ASP
TTATCAAATGGAGTTAGTGTCTTAACCAGCAAAGTGTTAGACCTCAAAAACTATATAGAT
AATAGTTTACCTCAATCACAGAATTGGTCGTTTCACAATCTGGAGTTTTGATATATCTA
          550            560            570            580            590            600

LYS GLN LEU LEU PRO ILE VAL ASN LYS GLN SER CYS ARG ILE SER ASN ILE GLU THR VAL
AAACAATTGTTACCTATTGTGAATAAGCAAAGCTGCAGAATATCAAATATCAAATATGAAACTGTG
TTTGTTAACAATGGATAACACTTATTCGTTTCGACGTCTTATAGTTTATAGTTTATATCTTTGACAC
          610            620            630            640            650            660

ILE GLU PHE GLN HIS LYS ASN ASN ARG LEU LEU GLU ILE THR ARG GLU PHE SER VAL ASN
ATAGAGTTCCAACAAAAGAACAACAGATTACTAGAGATTACCAGGAATTAGTGTTAAT
TATCTCAAGGTTGTTTTCTTGTTGTCTAATGATCTCTAATGGTCCCTTAAATCACAATTA
          670            680            690            700            710            720

ALA GLY VAL THR THR PRO VAL SER THR TYR MET LEU THR ASN SER GLU LEU LEU SER LEU
GCAGGTGTAACTACACCTGTAAGCACTTACATGTTAACTAATAGTGAATTATTGTCATTA
CGTCCACATTGATGTGGACATTCGTGAATGTACAATTGATTATCACTTAATAACAGTAAT
          730            740            750            760            770            780
```

FIG.3C.

```
ILE ASN ASP MET PRO ILE THR ASN ASP GLN LYS LYS LEU MET SER ASN ASN VAL GLN ILE
ATCAATGATATGCCTATAACAATGATCAGAAAAAGTTAATGTCCAACAATGTTCAAATA
TAGTTACTATACGGATATTGTTACTAGTCTTTTCAATTACAGTTGTTACAAGTTTAT
        790         800         810         820         830         840

VAL ARG GLN SER TYR SER ILE MET SER ILE ILE LYS GLU GLU VAL LEU ALA TYR VAL
GTTAGACAGCAAAGTTACTCTATCATGTCCATAATAAAAGAGGAAGTCTTAGCATATGTA
CAATCTGTCGTTTCAATGAGATAGTACAGGTATTATTTTCTCCTTCAGAATCGTATACAT
        850         860         870         880         890         900

VAL GLN LEU PRO LEU TYR GLY VAL ILE ASP THR PRO CYS TRP LYS LEU HIS THR SER PRO
GTACAATTACCACTATATGGTGTGATAGATACACCTGTTGGAAATTACACACATCCCT
CATGTTAATGGTGATATACCACTATCTATGTGGACAACCTTTAATGTGTAGGGA
        910         920         930         940         950         960

LEU CYS THR THR ASN THR LYS GLU GLY SER ASN ILE CYS LEU THR ARG THR ASP ARG GLY
CTATGTACAACAACAAAAGAAGGGTCAAACATCTGTTAACAAGAACTGACAGAGA
GATACATGTTGGTTGTTTCTTCCCAGTTTGTAGACAAATGTTCTTGACTGTCTCCT
        970         980         990        1000        1010        1020

TRP TYR CYS ASP ASN ALA GLY SER VAL SER PHE PHE PRO GLN ALA GLU THR CYS LYS VAL
TGGTACTGTGACAATGCAGGATCAGTATCTTTCTTCCCACAAGCTGAAACATGTAAAGTT
ACCATGACACTGTTACGTCCTAGTCATAGAAAGAAGGGTGTTCGACTTTGTACATTCAA
       1030        1040        1050        1060        1070        1080

GLN SER ASN ARG VAL PHE CYS ASP ILE PHE MET ASN SER LEU PRO SER GLU VAL ASN
CAATCGAATCGAGTATTTGTGACACAATGAACAGTTAACATTACCAAGTGAAGTAAAT
GTTAGCTTAGCTCATAAAACACTGTTACTGTTCAAATTGTAATGGTTCACTTCATTTA
       1090        1100        1110        1120        1130        1140

LEU CYS ASN VAL ASP ILE PHE ASN PRO LYS TYR ASP CYS LYS ILE MET THR SER LYS THR
CTCTGCAATGTTGACATATTCAATCCCAAATATGATTGTAAATTATGACTTCAAAACA
GAGACGTTACAACTGTATAAGTTAGGGTTTATACTAACATTTTAATACTGAAGTTTTGT
       1150        1160        1170        1180        1190        1200
```

FIG.3D.

```
ASP VAL SER SER SER VAL ILE THR SER LEU GLY ALA ILE VAL SER CYS TYR GLY LYS THR
GATGTAAGCAGCTCCGTTATCACATCTCTAGGAGCCATTGTGTCATGCTATGCAAAACT
CTACATTCGTCGAGGCAATAGTGTAGAGATCCTCGGTAACACAGTACGATACCGTTTGA
     1210      1220      1230      1240      1250      1260

LYS CYS THR ALA SER ASN LYS ASN ARG GLY ILE ILE LYS THR PHE SER ASN GLY CYS ASP
AAATGTACAGCATCCAATAAAAATCGTGGAATCATAAAGACATTTCTAACGGGTGTGAT
TTTACATGTCGTAGGTTATTTTTAGCACCTTAGTATTTCTGTAAAGATTGCCCACACTA
     1270      1280      1290      1300      1310      1320

TYR VAL SER ASN LYS GLY VAL ASP THR VAL SER VAL GLY ASN THR LEU TYR TYR VAL ASN
TATGTATCAAATAAAGGGTGGACACTGTGTCTGTAGGTAACACATTATATTATGTAAAT
ATACATAGTTTATTTCCCACCTGTGACACAGACATCCATTGTGTAATATAATACATTTA
     1330      1340      1350      1360      1370      1380

LYS GLN GLU GLY LYS SER LEU TYR VAL LYS GLY GLU PRO ILE ILE ASN PHE TYR ASP PRO
AAGCAAGAAGGCAAAAGTCTCTATGTAAAAGGTGAACCAATAAJAAATTCTATGACCCA
TTCGTTCTTCCGTTTTCAGAGATACATTTCCACTTGGTTATTATTTAAAGATACTGGGT
     1390      1400      1410      1420      1430      1440

LEU VAL PHE PRO SER ASP GLU PHE ASP ALA SER ILE SER GLN VAL ASN GLU LYS ILE ASN
TTAGTATTCCCCTCTGATGAATTTGATGCATCAATATCTCAAGTCAATGAGAAGATTAAC
AATCATAAGGGGAGACTACTTAAACTACGTAGTTATAGAGTTCAGTTACTCTTCTAATTG
     1450      1460      1470      1480      1490      1500

GLN SER LEU ALA PHE ILE ARG LYS SER ASP GLU LEU LEU HIS ASN VAL ASN ALA GLY LYS
CAGAGTTTAGCATTTATTCGTAAATCCGATGAATTATTACATAATGTAAATGCTGGTAAA
GTCTCAAATCGTAAATAAGCATTTAGGCTACTTAATAATGTATTACATTTACGACCATTT
     1510      1520      1530      1540      1550      1560

SER THR THR ASN ILE MET Thr Stop Stop Stop Bam HI
TCAACCACAAATATCATGACTTGATAATGAGGATCC
AGTTGGTGTTTATAGTACTGAACTATTACTCCTAGG
     1570
```

FIG.8

```
401  TTGGGGACCC  TTGATTGTTC  TTTCTTTTTC  GCTATTGTAA  AATTCATGTT
451  ATATGGAGGG  GGCAAAGTTT  TCAGGGTGTT  GTTTAGAATG  GGAAGATGTC
501  CCTTGTATCA  CCATGGACCC  TCATGATAAT  TTTGTTTCTT  TCACTTTCTA
551  CTCTGTTGAC  AACCATTGTC  TCCTCTTATT  TTCTTTTCAT  TTTCTGTAAC
601  TTTTCGTTA   AACTTTAGCT  TGCATTTGTA  ACGAATTTTT  AAATTCACTT
651  TTGTTTATTT  GTCAGATTGT  AAGTACTTTC  TCTAATCACT  TTTTTTTCAA
701  GGCAATCAGG  GTATATTATA  TTGTACTTCA  GCACAGTTTT  AGAGAACAAT
751  TGTTATAATT  AAATGATAAG  GTAGAATATT  TCTGCATATA  AATTCTGGCT
801  GGCGTGGAAA  TATTCTTATT  GGTAGAAACA  ACTACATCCT  GGTCATCATC
851  CTGCCTTTCT  CTTTATGGTT  ACAATGATAT  ACACTGTTTG  AGATGAGGAT
901  AAAATACTCT  GAGTCCAAAC  CGGGCCCCCTC  TGCTAACCAT  GTTCATGCCT
951  TCTTCTTTTT  CCTACAG                                GTGAGT
```

NUCLEIC ACID RESPIRATORY SYNCYTIAL VIRUS VACCINES

FIELD OF INVENTION

The present invention is related to the field of Respiratory Syncytial Virus (RSV) vaccines and is particularly concerned with vaccines comprising nucleic acid sequences encoding the fusion (F) protein of RSV.

BACKGROUND OF INVENTION

Respiratory syncytial virus (RSV), a negative-strand RNA virus belonging to the Paramyxoviridae family of viruses, is the major viral pathogen responsible for bronchiolitis and pneumonia in infants and young children (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Acute respiratory tract infections caused by RSV result in approximately 90,000 hospitalizations and 4,500 deaths per year in the United states (ref. 2). Medical care costs due to RSV infection are greater than $340 M annually in the United States alone (ref. 3). There is currently no licensed vaccine against RSV. The main approaches for developing an RSV vaccine have included inactivated virus, live-attenuated viruses and subunit vaccines.

The F protein of RSV is considered to be one of the most important protective antigens of the virus. There is a significant similarity (89% identity) in the amino acid sequences of the F proteins from RSV subgroups A and B (ref. 3) and anti-F antibodies can cross-neutralize viruses of both subgroups as well as protect immunized animals against infection with viruses from both subgroups (ref. 4). Furthermore, the F protein has been identified as a major target for RSV-specific cytotoxic T-lymphocytes in mice and humans (ref. 3 and ref. 5).

The use of RSV proteins as vaccines may have obstacles. Parenterally administered vaccine candidates of these types have proven poorly immunogenic with regard to the induction of neutralizing antibodies in seronegative humans or chimpanzees. The serum antibody response induced by these antigens may be further diminished in the presence of passively acquired antibodies, such as the transplacentally acquired maternal antibodies which most young infants possess. A subunit vaccine candidate for RSV consisting of purified fusion glycoprotein from RSV infected call cultures and purified by imunoaffinity or ion-exchange chromatography has bean described (ref. 6). Parenteral immunization of seronegative or seropositive chimpanzees with this preparation was performed and three doses of 50 μg were required in seronegative animals to induce RSV serum neutralizing titre of approximately 1:50. Upon, subsequent challenge of these animals with wild-type RSV, no affect of immunization on virus shedding or clinical disease could be detected in the upper respiratory tract. The effect of immunization with this vaccine on virus shedding in the lower respiratory tract was not investigated, although this is the site where the serum antibody induced by parenteral immunization may be expected to have its greatest effect.

Ten safety and immunogenicity studies have been performed in a small number of seropositive individuals. This vaccine was found to be safe in seropositive children and in three seronegative children (all >2.4 years of age). The effects of immunization on lower respiratory disease could not be determined because of the small number of children immunized. One immunizing dose in seropositive children induced a 4-fold increase in virus neutralizing antibody titres in 40 to 60% of the vaccinees. Thus, insufficient information is available from these small studies to evaluate the efficacy of this vaccine against RSV-induced disease. A further problem facing subunit RSV vaccines is the possibility that inoculation of seronegative subjects with immunogenic preparations might result in disease enhancement (sometimes referred to as immunopotentiation), similar to that seen in formalin inactivated RSV vaccines. In some studies, the immune response to immunization with RSV F protein or a synthetic RSV FG fusion protein resulted in a disease enhancement in rodents resembling that induced by a formalin-inactivated RSV vaccine. The association of immunization with disease enhancement using non-replicating antigens suggests caution in their use as vaccines in seronegative humans.

Live attenuated vaccine against disease caused by RSV may be promising for two main reasons. First, infection by a live vaccine virus induces a balanced immune response comprising mucosal and serum antibodies and cytolytic T-lymphocytes. Second, primary infection of infants with live attenuated vaccine candidates or naturally acquired wild-type virus is not associated with enhanced disease upon subsequent natural reinfection. It will be challenging to produce live attenuated vaccines that are immunogenic for younger infants who possess maternal virus-neutralizing antibodies and yet are attenuated for seronegative infants greater than or equal to 6 months. Attenuated live virus vaccines also have the risks of residual virulence and genetic instability.

Injection of plasmid DNA containing sequences encoding a foreign protein has been shown to result in expression of the foreign protein and the induction of antibody and cytotoxic T-lymphocyte responses to the antigen in a number of studies (see, for example, refs. 7, 8, 9). The use of plasmid DNA inoculation to express viral proteins for the purpose of immunization may offer several advantages over the strategies summarized above. Firstly, DNA encoding a viral antigen can be introduced in the presence of antibody to the virus itself, without loss of potency due to neutralization of virus by the antibodies. Secondly, the antigen expressed in vivo should exhibit a native conformation and, therefore, should induce an antibody response similar to that induced by the antigen present in the wild-type virus infection. In contrast, processes used in purification of proteins can induce conformational changes which may result in the loss of immunogenicity of protective epitopes and possibly immunopotentiation. Thirdly, the expression of proteins from injected plasmid DNAs can be detected in vivo for a considerably longer period of time than that in virus-infected cells, and this has the theoretical advantage of prolonged cytolytic T-cell and enhanced antibody responses. Fourthly, in vivo expression of antigen may provide protection without the need for extrinsic adjuvant.

The ability to immunize against disease caused by RSV by administration of a DNA molecule encoding an RSV F protein was unknown before the present invention. In particular, the efficacy of immunization against RSV induced disease using a gene encoding a secreted form of the RSV F protein was unknown. It would be useful and desirable to provide isolated genes encoding RSV F protein and vectors for in vivo administration for use in immunogenic preparations, including vaccines, for protection against disease caused by RSV and for the generation of diagnostic reagents and kits. In particular, it would be desirable to provide vaccines that are immunogenic and protective in humans, including seronegative infants, that do not cause disease enhancement.

SUMMARY OF INVENTION

The present invention relates to a method of immunizing a host against disease caused by respiratory syncytial virus, to nucleic acid molecules used therein, and to diagnostic procedures utilizing the nucleic acid molecules. In particular, the present invention is directed towards the provision of nucleic acid respiratory syncytial virus vaccines.

In accordance with one aspect of the invention, there is provided a vector, comprising:

a first nucleotide sequence encoding a RSV F protein or a protein capable of generating antibodies that specifically react with RSV F protein;

a promoter sequence operatively coupled to the first nucleotide sequence for expression of the RSV F protein, and a second nucleotide sequence located adjacent the first nucleotide sequence to enhance the immunoprotective ability of the RSV F protein when expressed in vivo from the vector in a host.

The first nucleotide sequence may be that which encodes a full-length RSV F protein, as seen in FIG. 2 (SEQ ID No: 2). Alternatively, the first nucleotide sequence may be that which encodes a RSV F protein from which the transmembrane region is absent. The latter embodiment may be provided by a nucleotide sequence which encodes a full-length RSV F protein but contains a translational stop codon immediately upstream of the start of the transmembrane coding region, thereby preventing expression of a transmembrane region of the RSV F protein, an seen in FIG. 3 (SEQ. ID No. 4). The lack of expression of the transmembrane region results in a secreted form of the RSV F protein.

The second nucleotide sequence may comprise a pair of splice sites to prevent aberrant mRNA splicing, whereby substantially all mRNA encodes the RSV protein. Such second nucleotide sequence may be located between the first nucleotide sequence and the promoter sequence.

Such second nucleotide sequence preferably is that of rabbit β-globin intron II, as shown in FIG. 8 (SEQ ID No: 5).

A vector encoding the F protein and provided by this aspect of the invention may specifically be pXL2 or pXL4, as seen in FIGS. 5 or 7.

The promoter sequence preferably is an immediate early cytomegalovirus (CMV) promoter. Such cytomegalovirus promoter has not previously been employed in vectors containing nucleotide sequences encoding an RSV F protein. Accordingly, in another aspect of the invention, there is provided a vector, comprising:

a first nucleotide sequence encoding a RSV F protein or a protein capable of generating antibodies that specifically react with RSV F protein, and a cytomegalovirus promoter operatively coupled to the first nucleotide sequence for expression of the RMV F protein.

The first nucleotide sequence may be any of the alternatives described above. The second nucleotide sequence described above also may be present in a vector provided in accordance with this second aspect of the invention.

Certain of the vectors provided herein may be used to immunize a host against RSV infection or disease using RSV F protein lacking a transmembrane region. In accordance with a further aspect of the present invention, therefore, there is provided a method of immunizing a host against disease caused by infection with respiratory syncytial virus, which comprises administering to the host an effective amount of a vector comprising a first nucleotide sequence encoding an RSV F or on RSV F protein lacking a transmembrane region and a promoter sequence operatively coupled to the first nucleotide sequence for expression of the RSV F protein in the host, which may be a human host. The promoter preferably is an immediate early cytomegalovirus promoter.

The nucleotide sequence encoding the truncated RSV F protein may be that as described above.

A vector containing a second nucleotide, sequence located adjacent a first nucleotide sequence encoding an RSV F protein and effective to enhance the immunoprotective ability of the RSV F protein expressed by the first nucleotide sequence may be used to immunize a host. Accordingly, in an additional aspect of the present invention, there is provided a method of immunizing a host against disease caused by infection with respiratory syncytial virus (RSV), which comprises administering to the host an effective amount of a vector comprising a first nucleotide sequence encoding an RSV F protein or a protein capable of generating antibodies that specifically react with RSV F protein, a promoter sequence operatively coupled to the first nucleotide sequence for expression of the RSV F protein, and a second nucleotide sequence located adjacent the first sequence to enhance the immunoprotective ability of the RSV-F protein when expressed in vivo from said vector in said host. Specific vectors which may be used in this aspect of the invention are those identified as pXL2 and pXL4 in FIGS. 5 and 7.

The present invention also includes a novel method of using a gone encoding an RSV F protein or a protein capable of generating antibodies that specifically react with RSV F protein to protect a host against disease caused by infection with respiratory syncytial virus, which comprises:

isolating the gene, operatively linking the gene to at least one control sequence to produce a vector, said control sequence directing expression of the RSV F protein when introduced into a host to produce an immune response to the RSV F protein, and introducing the vector into a host.

The procedure provided in accordance with this aspect of the invention may further include the step of:

operatively linking the gene to an immunoprotection enhancing sequence to produce an enhanced immunoprotection to the RSV F protein in the host, preferably by introducing the immunoprotection enhancing sequence between the control sequence and the gene.

In addition, the present invention includes a method of producing a vaccine for protection of a host against disease caused by infection with respiratory syncytial virus, which comprises:

isolating a first nucleotide sequence encoding an RSV F protein or a protein capable of generating antibodies that specifically react with RSV F protein, operatively linking the first nucleotide sequence to at least one control sequence to produce a vector, the control sequence directing expression of the RSV F protein when introduced to a host to produce an immune response to the RSV F protein, and formulating the vector as a vaccine for in vivo administration to a host.

The first nucleotide sequence further may be operatively linked to a second nucleotide sequence to enhance the immunoprotective ability of the RSV F protein when expressed in vivo from the vector in a host. The vector may be selected from pXL1, pXL2 and pXL4. The invention further includes a vaccine for administration to a host, including a human host, produced by this method as wall an immunogenic compositions comprising an immunoeffective amount of the vectors described herein.

As noted previously, the vectors provided herein are useful in diagnostic applications. In a further aspect of the invention, therefore, there is provided a method of determining the presence of an RSV F protein in a sample, comprising the steps of:

(a) immunizing a host with a vector comprising a first nucleotide sequence encoding an RSV F protein or a protein capable of generating antibodies that specifically react with RSV F protein and a promoter sequence operatively coupled to the first nucleotide sequence for expression of the RSV F protein in the host to produce antibodies specific to the RSV F protein;

(b) isolating the RSV F protein specific antibodies;

(c) contacting the sample with the isolated antibodies to produce complexes comprising any RSV F protein present in a sample and the RSV F protein-specific antibodies; and (d) determining the production of the complexes.

The vector employed to elicit the antibodies may be pXL1, pXL2, pXL3 or pXL4.

The invention also includes a diagnostic kit for detecting the presence of an RSV F protein in a sample, comprising:

(a) a vector comprising a first nucleotide sequence encoding an RSV F protein capable of generating antibodies that specifically react with RSV F protein and a promoter sequence operatively coupled to said first nucleotide sequence for expression of said RSV F protein in a host immunized therewith;

(b) means for contacting the RSV F specific antibodies with the sample to produce a complex comprising any RSV F protein in the sample and RSV F protein specific antibodies, and (c) means for determining production of the complex.

The present invention is further directed to immunization wherein the polynucleotide is an RNA molecule which codes for an RSV F protein.

The present invention in further directed to a method for producing polyclonal antibodies comprising the use of the immunization method described herein, and further comprising the stop of isolating the polyclonal antibodies from the immunized animal.

The present invention is also directed to a method for producing monoclonal antibodies comprising the steps of:

(a) constructing a vector comprising:
a first nucleotide sequence encoding a RSV F protein;
a promoter sequence operatively coupled to said first nucleotide sequence for expression of said RSV F protein; and, optionally,
a second nucleotide sequence located adjacent said first nucleotide sequence to enhance the immunoprotective ability of said RSV F protein when expressed in vivo from said vector in a host.

(b) administering the vector to at least one mouse to produce at least one immunized mouse;

(c) removing B-lymphocytes from the at least one immunized mouse;

(d) fusing the B-lymphocytes from the at least one immunized mouse with mycloma cells, thereby producing hybridomas;

(e) cloning the hybridomas;

(f) selecting clones which produce anti-F protein antibody;

(g) culturing the anti-F protein antibody-producing clones; and then (h) isolating anti-F protein antibodies.

In this application, the term "RSV F protein" in used to define a full-length RSV F protein, secreted form of RSV F protein lacking a transmembrane region, such proteins having variations in their amino acid sequences including those naturally occurring in various strains of RSV, as well as functional analogs of the RSV F protein. In this application, a first protein is a "functional analog" of a second protein if the first protein is immunologically related to and/or has the same function as the second protein. The functional analog may be, for example, a fragment of the protein or a substitution, addition or deletion mutant thereof.

BRIEF DESCRIPTION OF THE FIGURES

The present invention will be further understood from the following general description and Examples with reference to the Figures in which:

FIG. 1 illustrates a restriction map of the gene encoding the F protein of Respiratory Syncytial virus;

FIGS. 2A, 2B, 2C, 2D and 2E show the nucleotide sequence of the gene encoding the membrane attached form of the F protein of Respiratory Syncytial Virus (SEQ ID No: 1) as well as the amino acid sequence of the RSV F protein encoded thereby (SEQ ID No: 2);

FIGS. 3A, 3B, 3C and 3D show the nucleotide sequence of the gene encoding the secreted form of the RSV F protein (SEQ ID No: 3) as wall an the amino acid sequence of the truncated RSV F protein encoded thereby (SEQ ID No: 4);

FIG. 8 shows the nucleotide sequence for the rabbit β-globin Intron II sequence (SEQ ID No. 5).

GENERAL DESCRIPTION OF INVENTION

As described above, the present invention relates generally to DNA immunization to obtain protection against infection by respiratory syncytial virus and to diagnostic procedures using particular vectors. In the present invention, several recombinant vectors are constructed to contain a nucleotide sequence encoding an RSV F protein.

The nucleotide sequence of the RSV F gene is shown in FIG. 2 (SEQ ID No: 1). Certain constructs provided herein include the nucleotide sequence encoding the full-length RSV-F protein while others include an RSV F gene modified by insertion of termination codons immediately upstream of the transmembrane coding region (see FIG. 3, SEQ ID No: 3), to prevent expression of the transmembrane portion of the protein and to produce a secreted or truncated RSV F protein.

The nucleotide sequence encoding the RSV F protein is operatively coupled to a promoter sequence for expression of the encoded RSV F protein. The promoter sequence may be the immediately early cytomegalovirus (CMV) promoter. This promoter is described in ref. 13. Any other convenient promoter may be used, including constitutive promoters, such as, Rous Sarcoma Virus LTRs, and inducible promoters, such as metallothionine promoter, and tissue specific promoters.

Figure 4A:
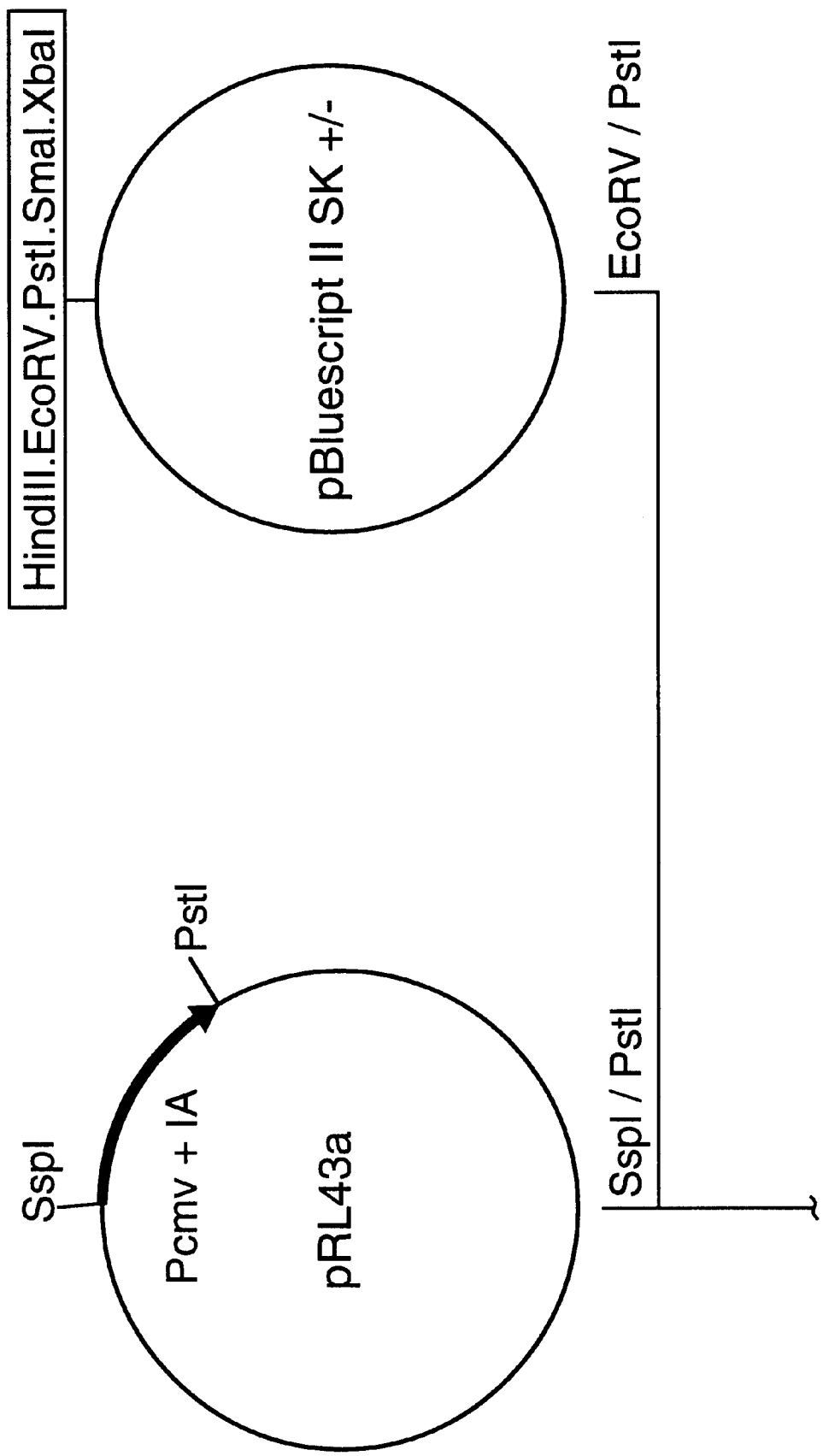
FIG. 4 shows the construction of plasmid pXL1 containing the gone encoding a secreted form of the RV F protein.
Figure 4B:
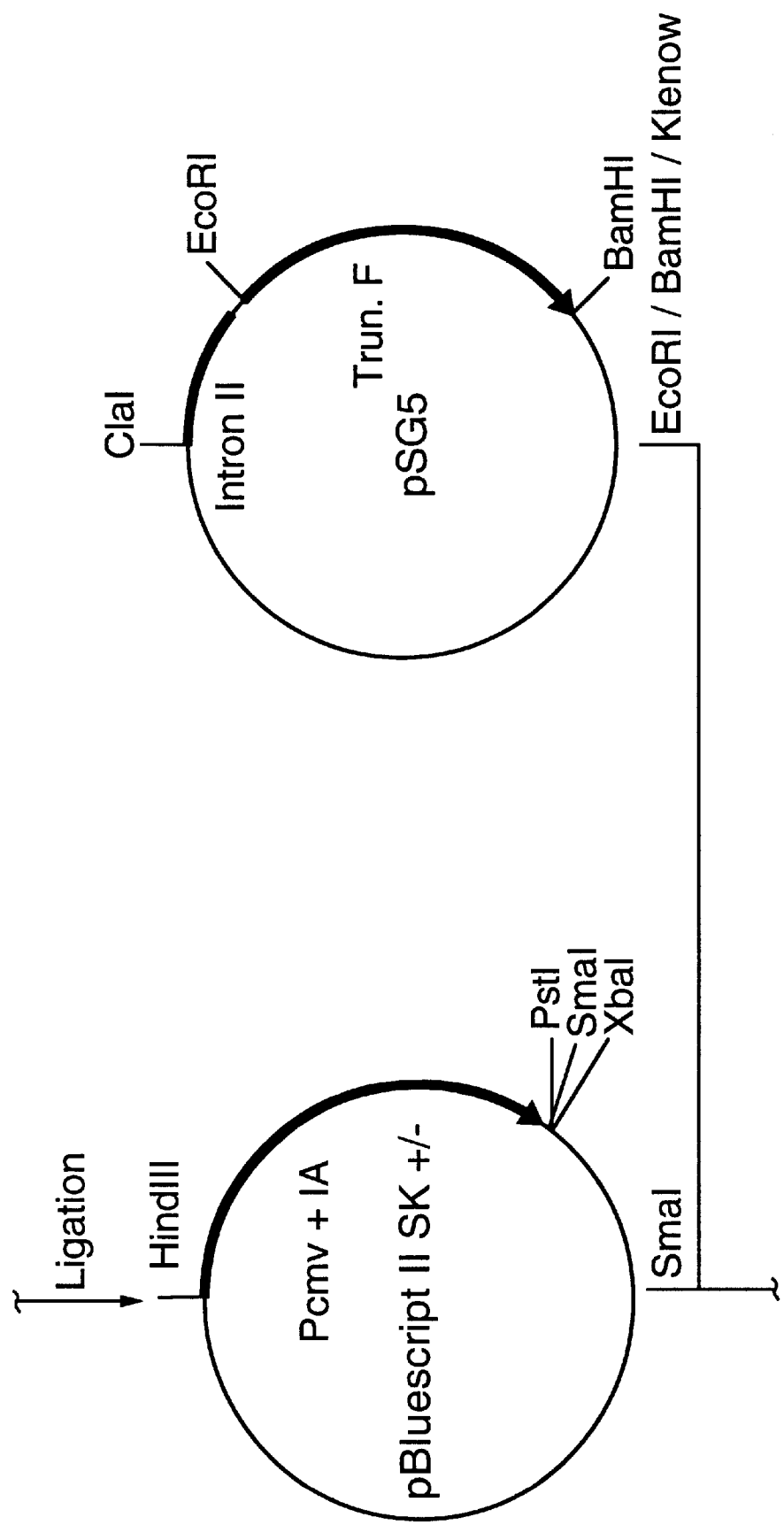
Figure 4C:
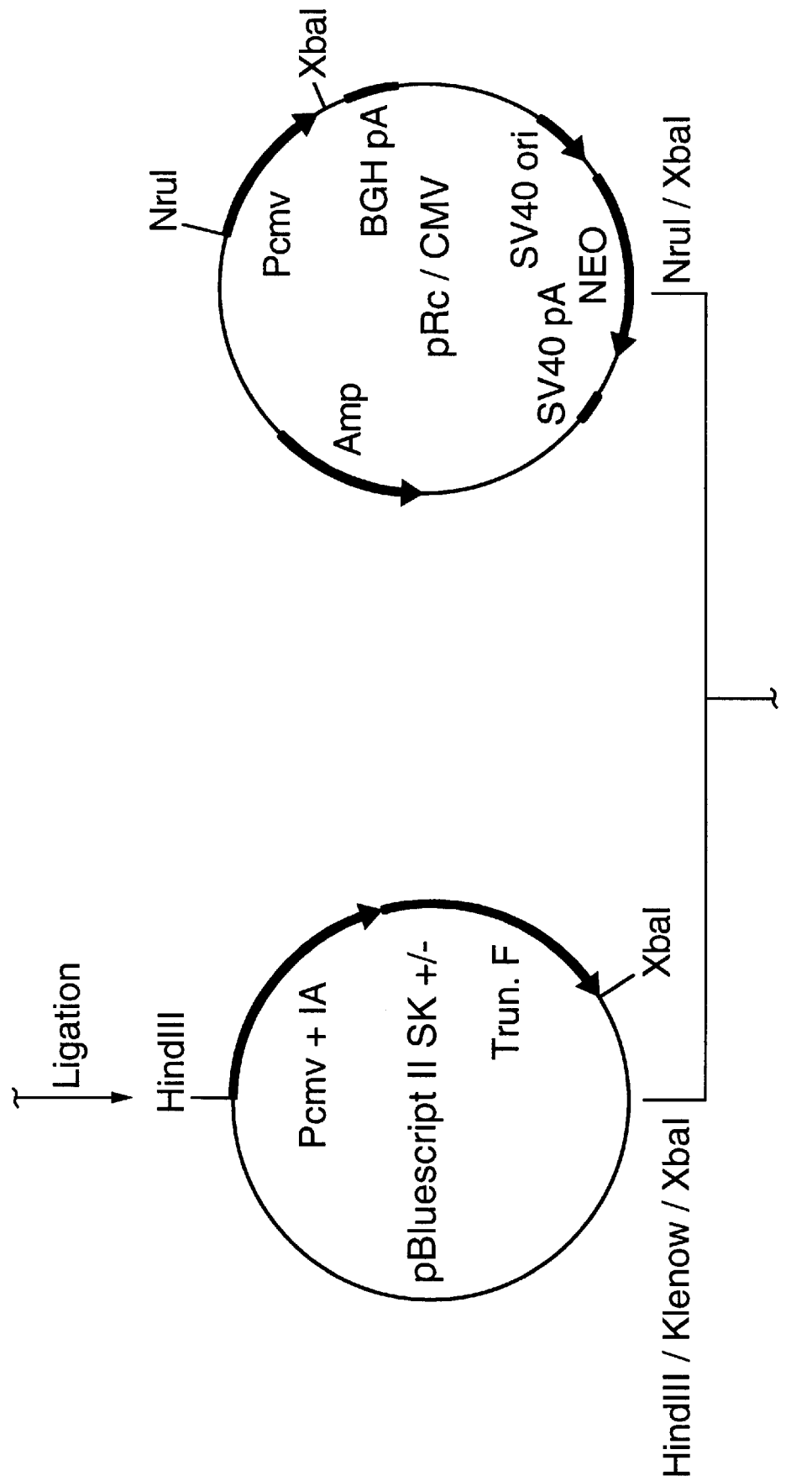
Figure 4D:
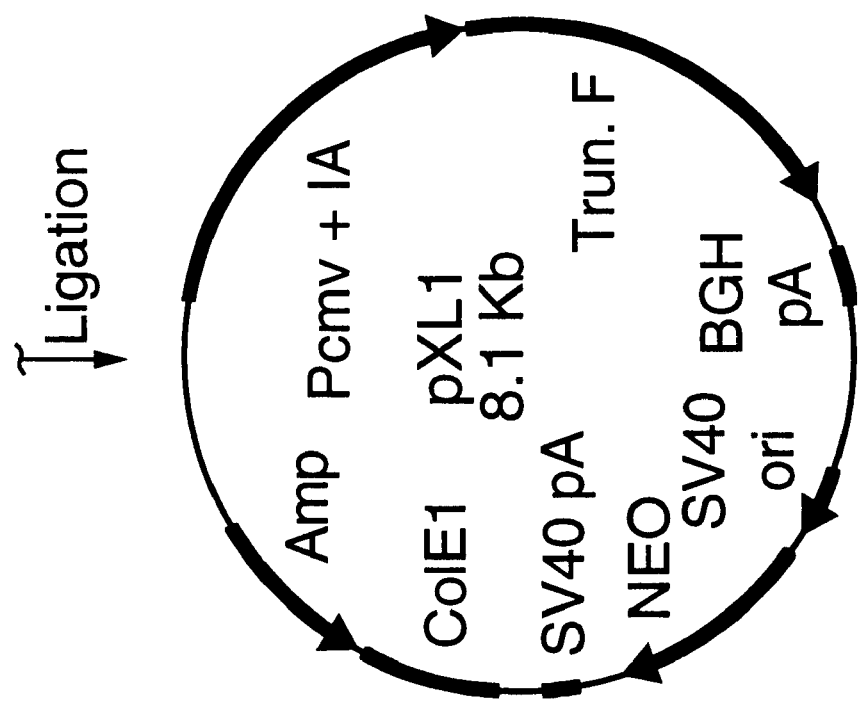

The vector, when administered to an animal, effects in vivo RSV F protein expression, as demonstrated by an antibody response in the animal to which it is administered. Such antibodies may be used herein in the detection of RSV protein in a sample, as described in more detail below. When the encoded RSV F protein is in the form of an RSV F protein from which the transmembrane region is absent, such as plasmid pXL1 (FIG. 4), the administration of the vector conferred protection in nice to challenge by live RSV, an seen from the Examples below.

The recombinant vector also may include a second nucleotide sequence located adjacent the RSV F protein encoding nucleotide sequence to enhance the immunoprotective ability of the RSV F protein when expressed in vivo in a host. Such enhancement may be provided by increased in vivo expression, for example, by increased mRNA stability, enhanced transcription and/or translation. This additional sequence preferably is located between the promoter sequence and the RSV F protein-encoding sequence.

This enhancement sequence may comprise a pair of splice sites to prevent aberrant mRNA splicing during transcription and translation so that substantially all mRNA encodes an RSV F protein. Specifically, rabbit β-globin Intron II sequence shown in FIG. 8 (SEQ ID No: 5) may provide such splice sites, as also described in ref. 15.

Figure 5A:
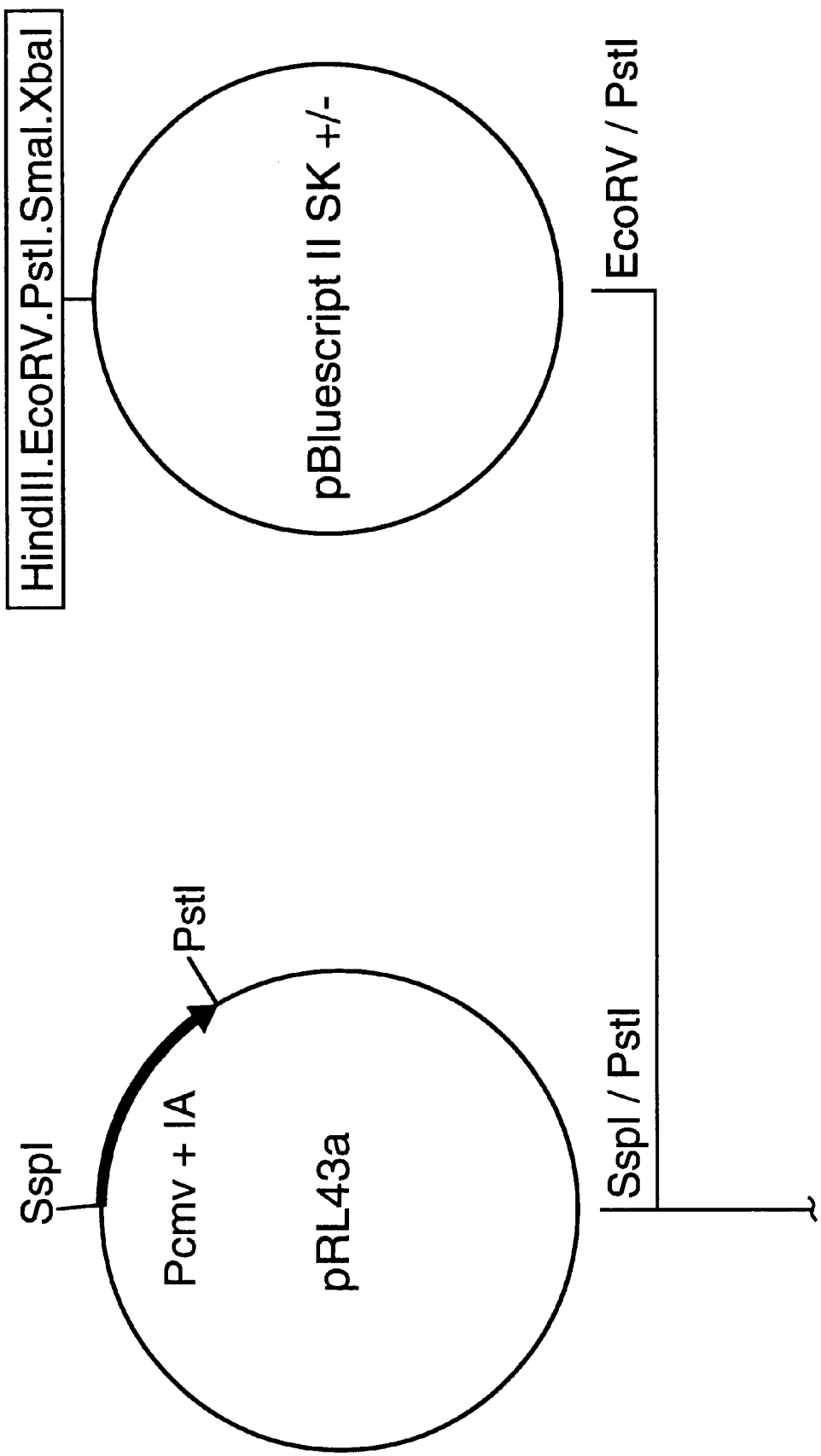
FIG. 5 shows the construction of plasmid pXL2 containing a gene encoding secreted form of the RSV F protein and containing the rabbit β-globin Intron II sequence.
Figure 5B:
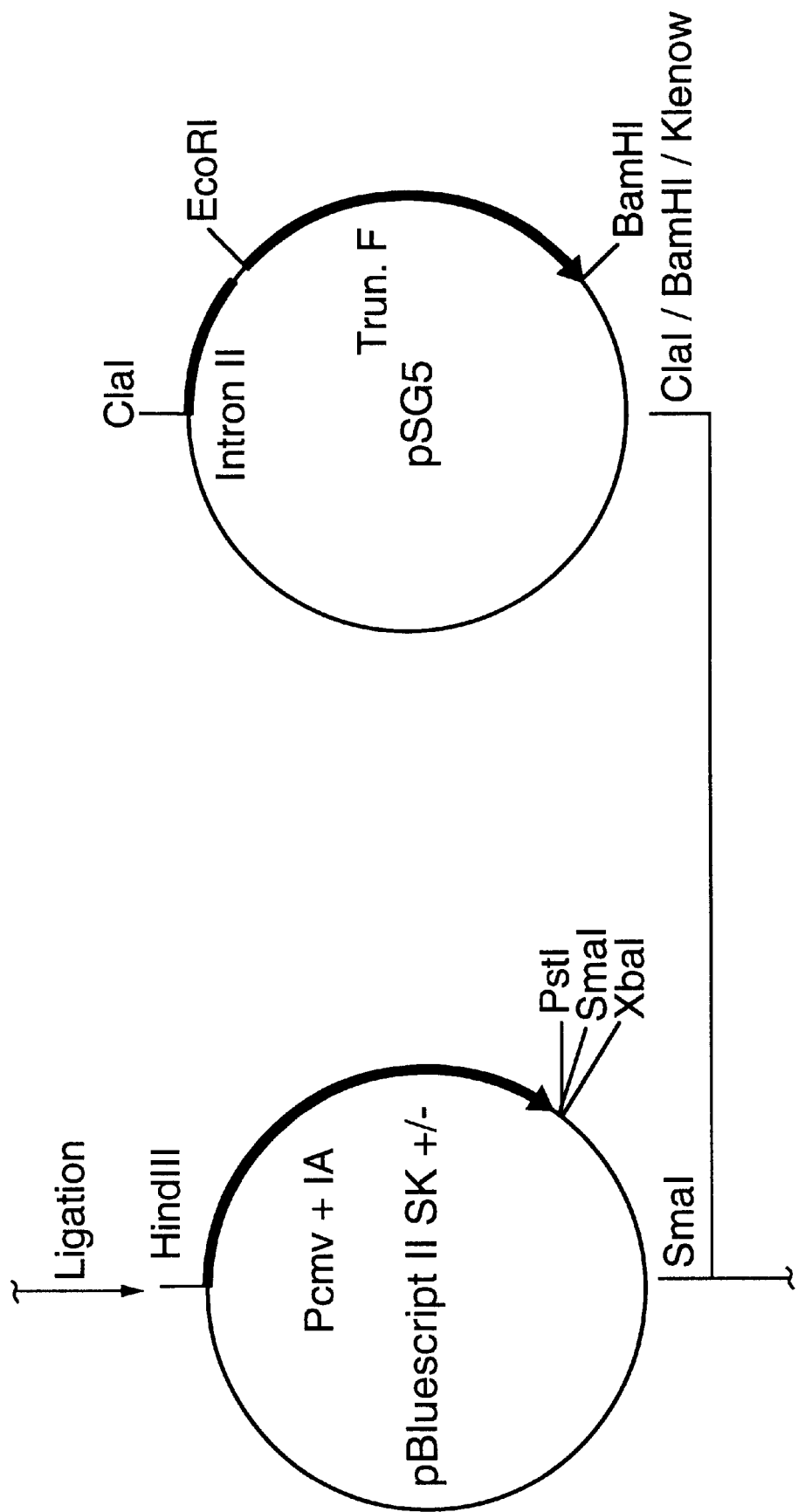
Figure 5C:
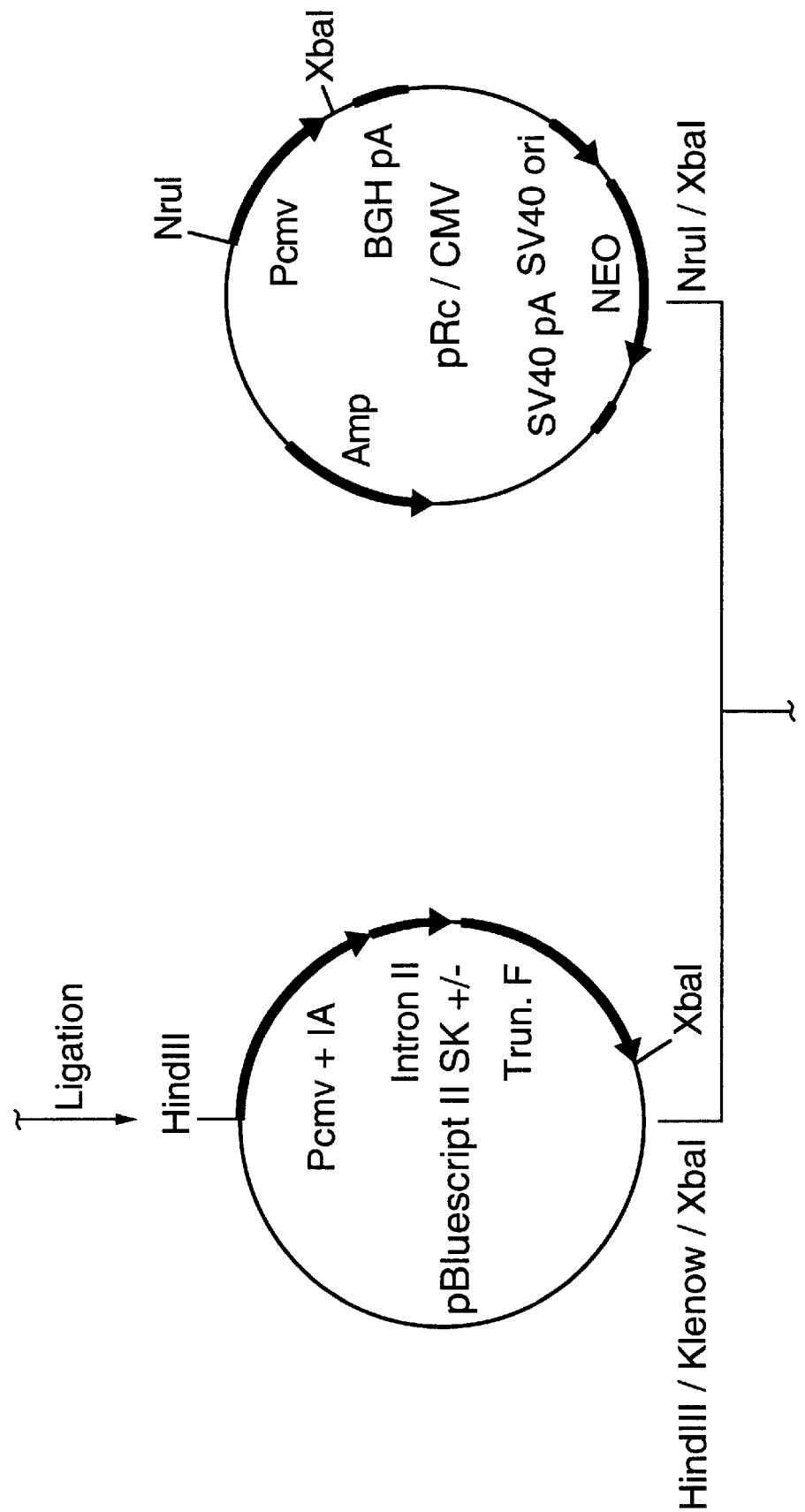
Figure 5D:
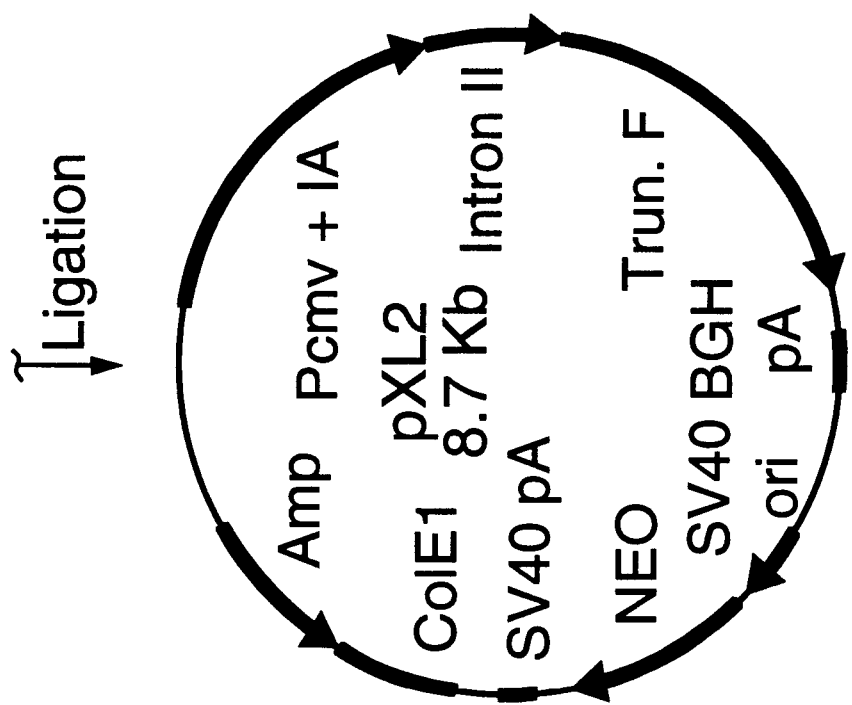
Figure 7A:
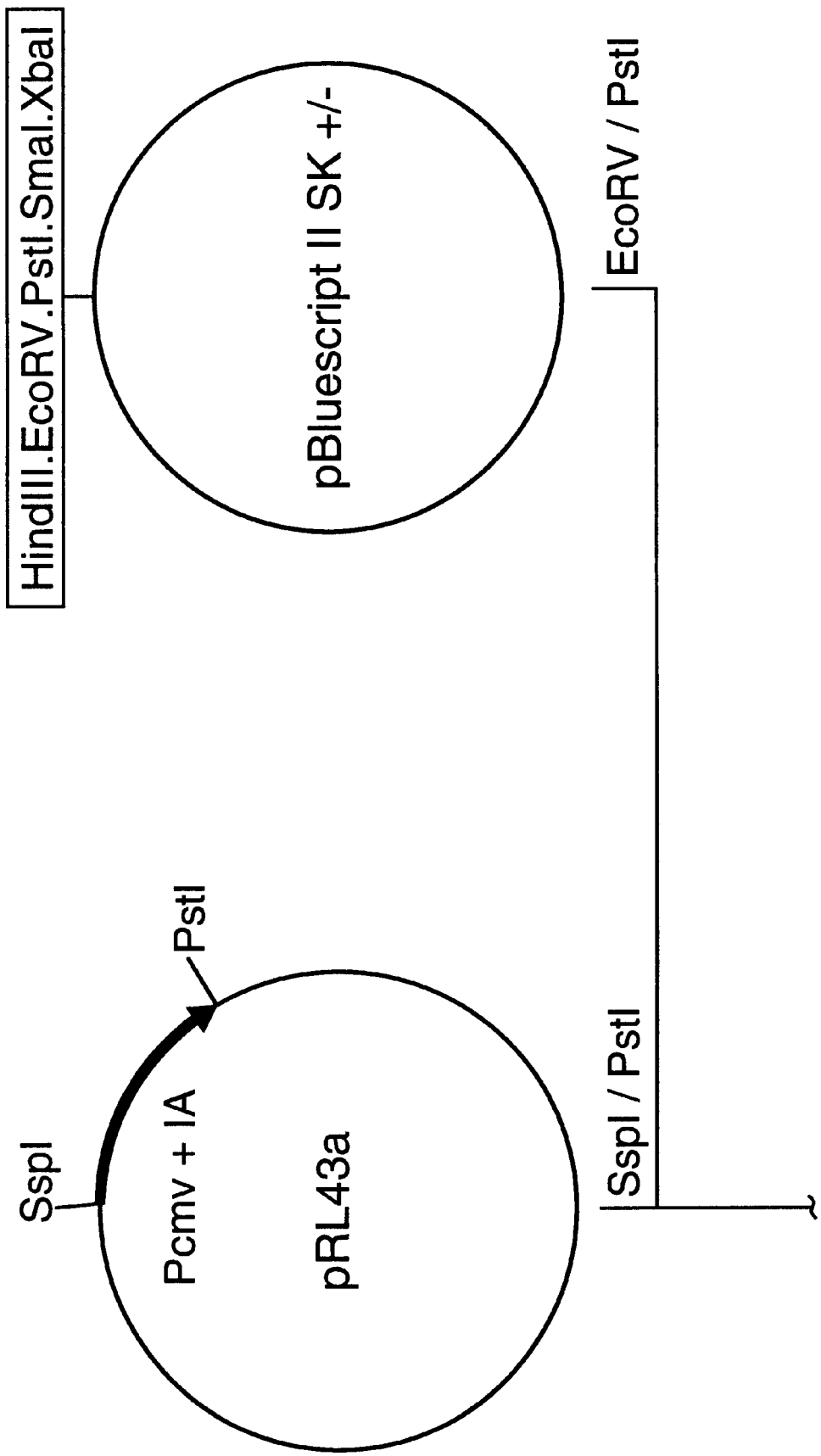
FIG. 7 shows the construction of plasmid pXL4 containing a gene encoding a membrane attached form of the RSV F protein and containing the rabbit β-globin Intron II sequence.
Figure 7B:
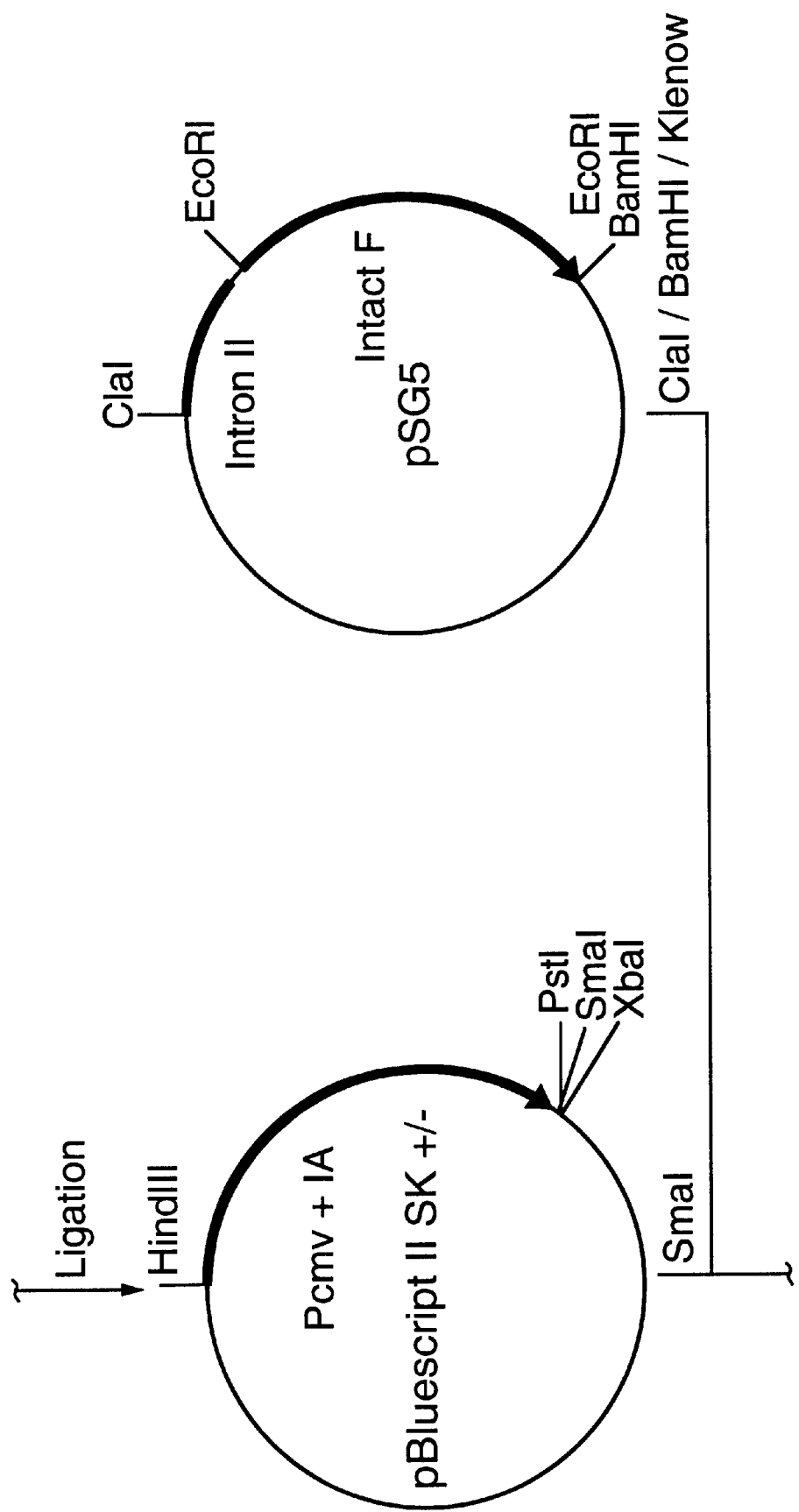
Figure 7C:
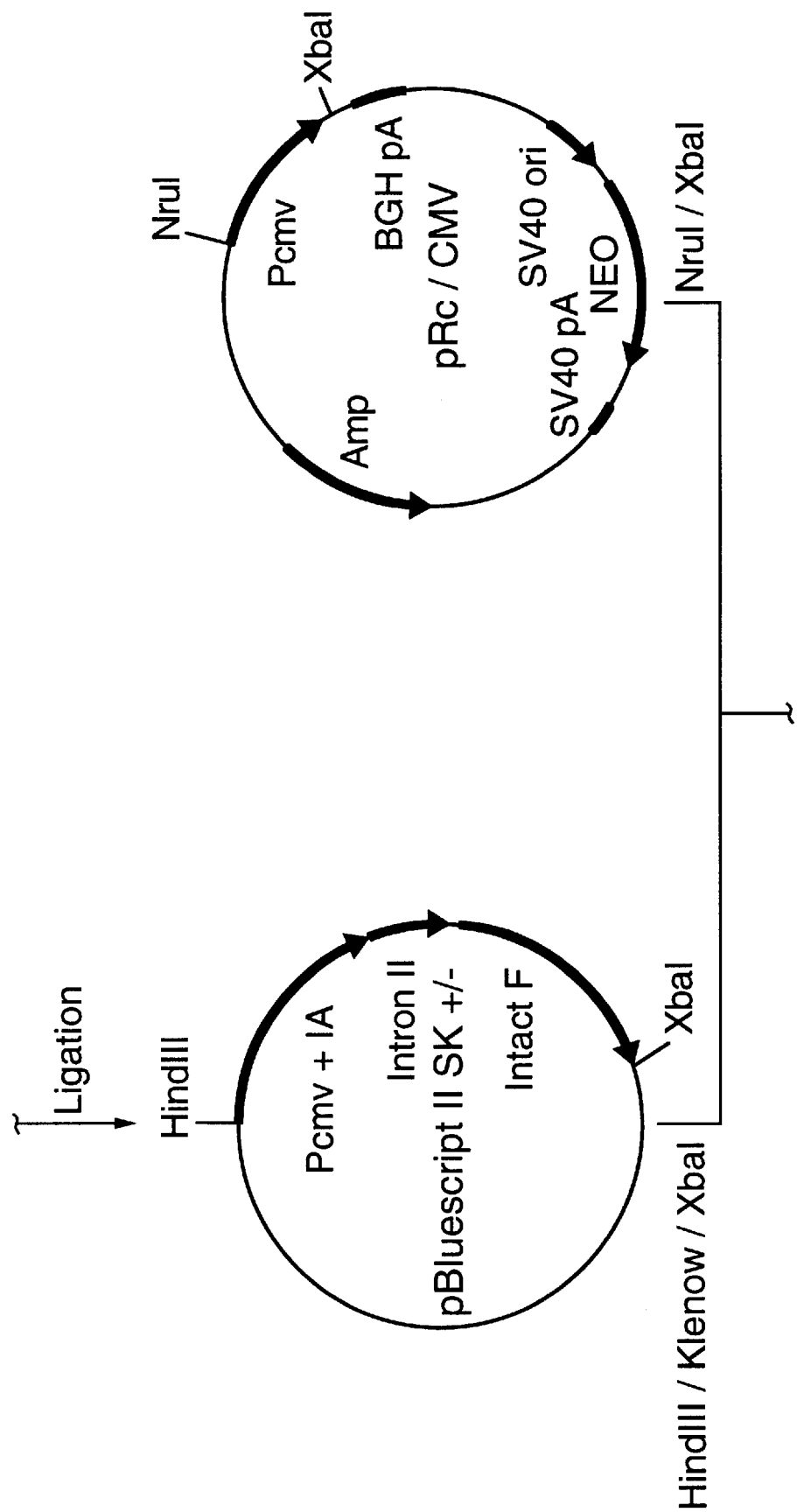
Figure 7D:
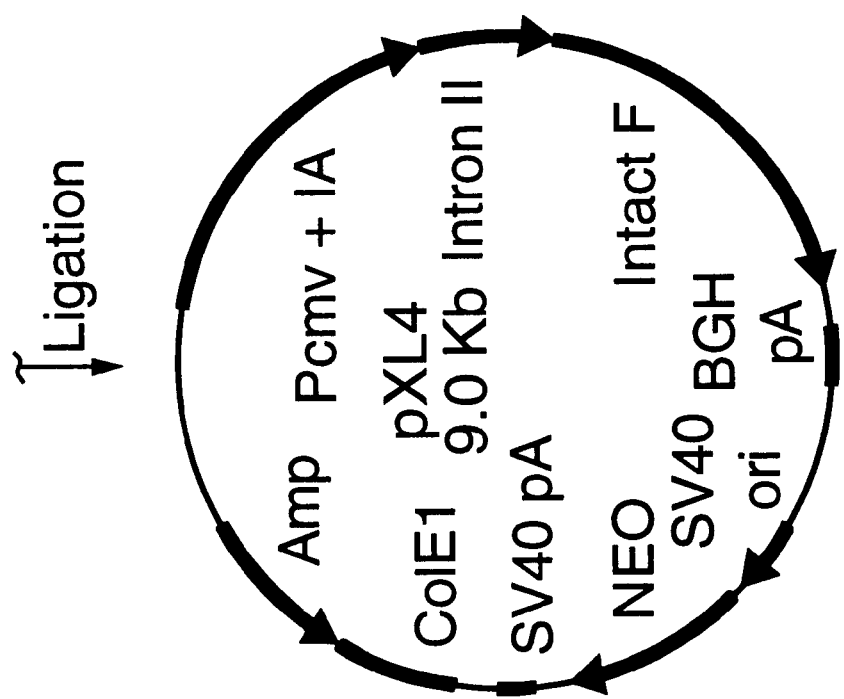

The constructs containing the Intron II sequence, CMV promoter and nucleotide sequence coding for the truncated RSV F protein, i.e. plasmid pXL2 (FIG. 5), induced complete protection in mice against challenge with live RSV, as seen in the Examples below, when the construct was administered in vivo. In addition, the constructs containing the Intron II sequence, CMV promoter and nucleotide sequence coding for the full-length RSV F protein, i.e. plasmid pXL4 (FIG. 7), also conferred protection in mice to challenge with live RSV, as seen from the Examples below.

The vector provided herein may also comprise a third nucleotide sequence encoding a further antigen from RSV, an antigen from at least one other pathogen or at least one immunomodulating agent, such as cytokine. Such vector may contain said third nucleotide sequence in a chimeric or a bicistronic structure. Alternatively, vectors containing the third nucleotide sequence may be separately constructed and coadministered to a host, with the nucleic acid molecule provided herein.

The vector may further comprise a nucleotide sequence encoding a heterologous signal peptide, such an human tissue plasminogen activator (TPA), in place of the endogenous signal peptide.

It is clearly apparent to one skilled in the art, that the various embodiments of the present invention have many applications in the fields of vaccination, diagnosis, treatment of, RSV infections. A further non-limiting discussion of such uses is further presented below.

1. Vaccine Preparation and Use

Immunogenic compositions, suitable to be used as vaccines, may be prepared from the RSV F genes and vectors as disclosed herein. The vaccine elicits an immune response in a subject which includes the production of anti-F antibodies. Immunogenic compositions, including vaccines, containing the nucleic acid may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 9324640, ref. 17) or the nucleic acid may be associated with an adjuvant, as described in more detail below. Liposomes comprising cationic lipids interact spontaneously and rapidly with polyanions such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lymosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moléculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactideco-glycolide). Other polymers for encapsulation are suggested, such as poly(glycolide), poly(DL-lactide-coglycolide), copolyoxalates, polycaprolactone, poly(lactide-co-caprolactone), poly(esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The RSV F genes and vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection site with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as, for example, pharmaceutical grades of saccharine, cellulose and magnesium carbonate. These compositions can take the form of solutions, suspensions, tablets, pills, capsules, sustained release formulations or powders and contain about 1 to 95% of the RSV F genes and vectors.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the RSV F protein and antibodies thereto, and if needed, to produce a cell-mediated immune response. Precise amounts of active ingredient required to be administered depend on the judgment of the practitioner. However, suitable dosage ranges are readily determinable by one skilled in the art and may be of the order of about 1 µg to about 1 mg of the RSV F genes and vectors. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immunomodulating material can provoke potent immune responses to antigens. These include saponins complexed to membrane protein antigens to produce immune stimulating complexes (TSCOMS), pluronic polymers with mineral oil, killed mycobacteria in mineral oil, Freund's complete adjuvant, bacterial products, such as muramyl dipeptide (MDP) and lipopolysaccharide (LPS), as wall as monophoryl lipid A, QS 21 and polyphosphazene.

In particular embodiments of the present invention, the vector comprising a first nucleotide sequence encoding an F protein of RSV may be delivered in conjunction with a targeting molecule to target the vector to selected cells including cells of the immune system.

The polynucleotide may be delivered to the host by a variety of procedures, for example, Tang et al. (ref. 10) disclosed that introduction of gold microprojectiles coated with DNA encoding bovine growth hormone (BGH) into the skin of mice resulted in production of anti-BGH antibodies in the mice, while Furth at al. (ref. 11) showed that a jet injector could be used to transfect skin, muscle, fat and mammary tissues of living animals.

2. Immunoassays

The RSV F genes and vectors of the present invention are useful as immunogens for the generation of anti-F antibodies for use in immunoassays, including enzyme-linked immunosorbent assays (ELISA), RIAs and other non-enzyme linked antibody binding assays or procedures known in the art. In ELISA assays, the vector first is administered to a host to generate antibodies specific to the RSV F protein. These RSV F-specific antibodies are immobilized onto a selected surface, for example, a surface capable of binding the antibodies, such as the wells of a polystyrene microtiter plate. After washing to remove incompletely adsorbed antibodies, a non-specific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound RSV F specific antibodies, and subsequent washing, the occurrence, and even amount, of immunocomplex formation may be determined.

BIOLOGICAL MATERIALS

Certain plasmids that contain the gene encoding RSV F protein and referred to herein have been deposited with the America Type Culture Collection (ATCC) located at 12301 Parklawn Drive, Rockville, Md., 20852, U.S.A., pursuant to the Budapest Treaty and prior to the filing of this application.

Samples of the deposited plasmids will become available to the public upon grant or a patent based upon this United States patent application. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

| Plasmid | ATCC Designation | Date Deposited |
|---------|------------------|----------------|
| pXL1    | 97167            | May 30, 1995   |
| pXL2    | 97168            | May 30, 1995   |
| pXL3    | 97169            | May 30, 1995   |
| pXL4    | 97170            | May 30, 1995   |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents art contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

EXAMPLE 1

This Example describes the construction of vectors containing the RSV F gene.

FIG. 1 shows a restriction map of the gene encoding the F protein of Respiratory Syncytial Virus and FIG. 2 shows the nucleotide sequence of the gene encoding the full-length RSV F protein (SEQ ID No: 1) and the deduced amino acid sequence (SEQ ID No: 2). FIG. 3 shows the gene encoding the secreted RSV F protein (SEQ ID No: 3) and the deduced amino acid sequence (SEQ ID No: 4).

Figure 6A:
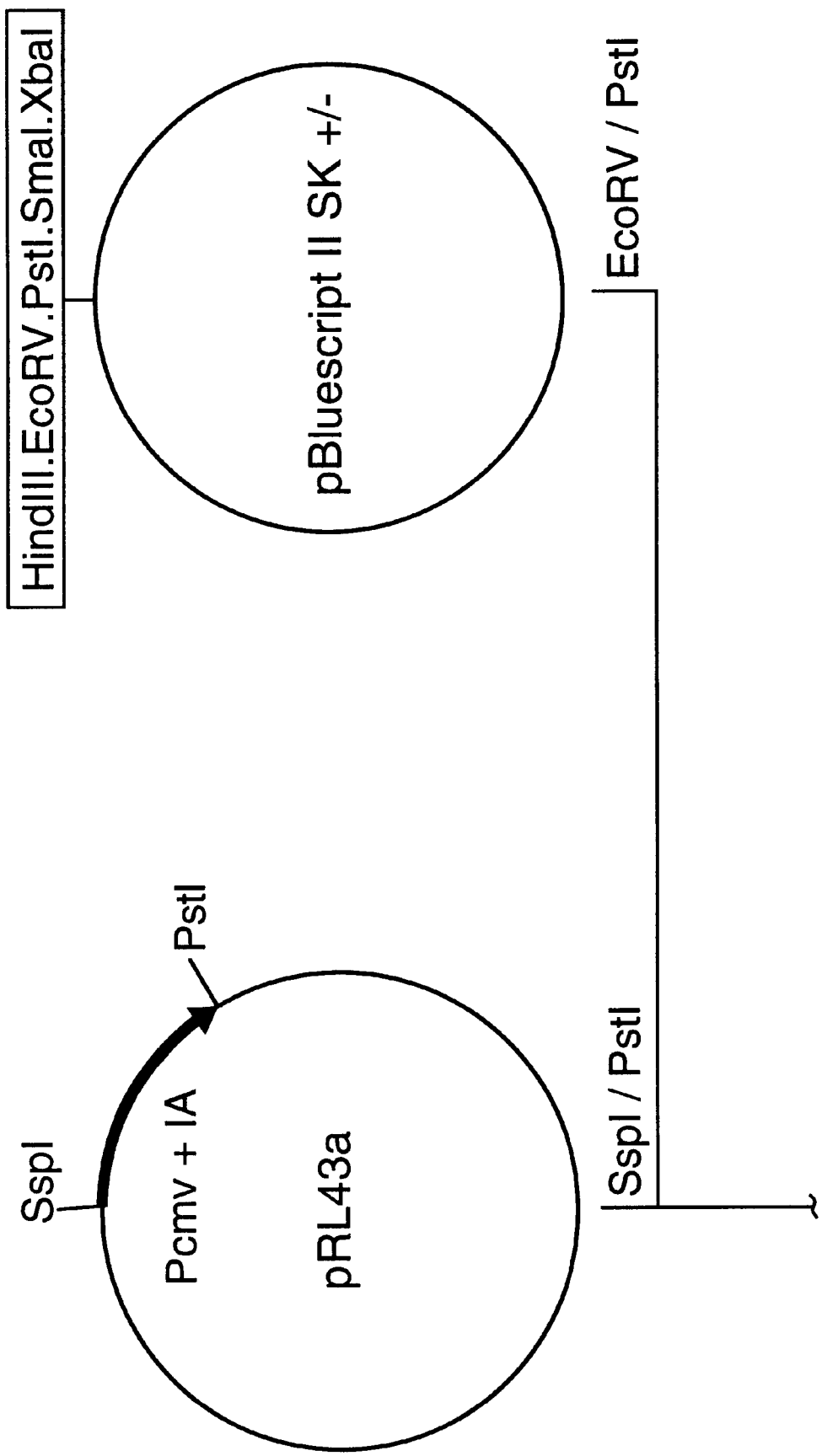
FIG. 6 shows the construction of plasmid pXL3 containing the gene encoding a membrane attached form of the RSV F protein.
Figure 6B:
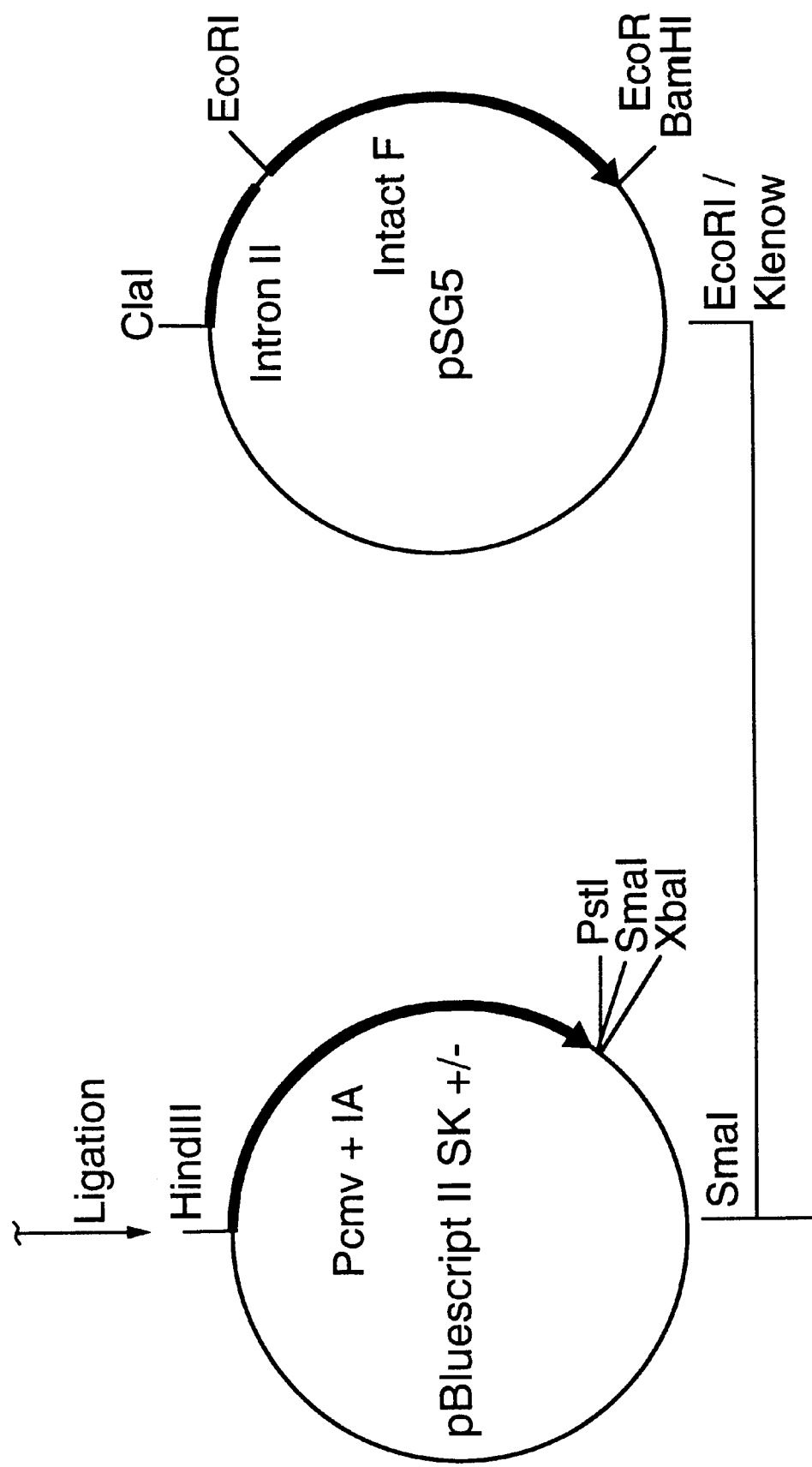
Figure 6C:
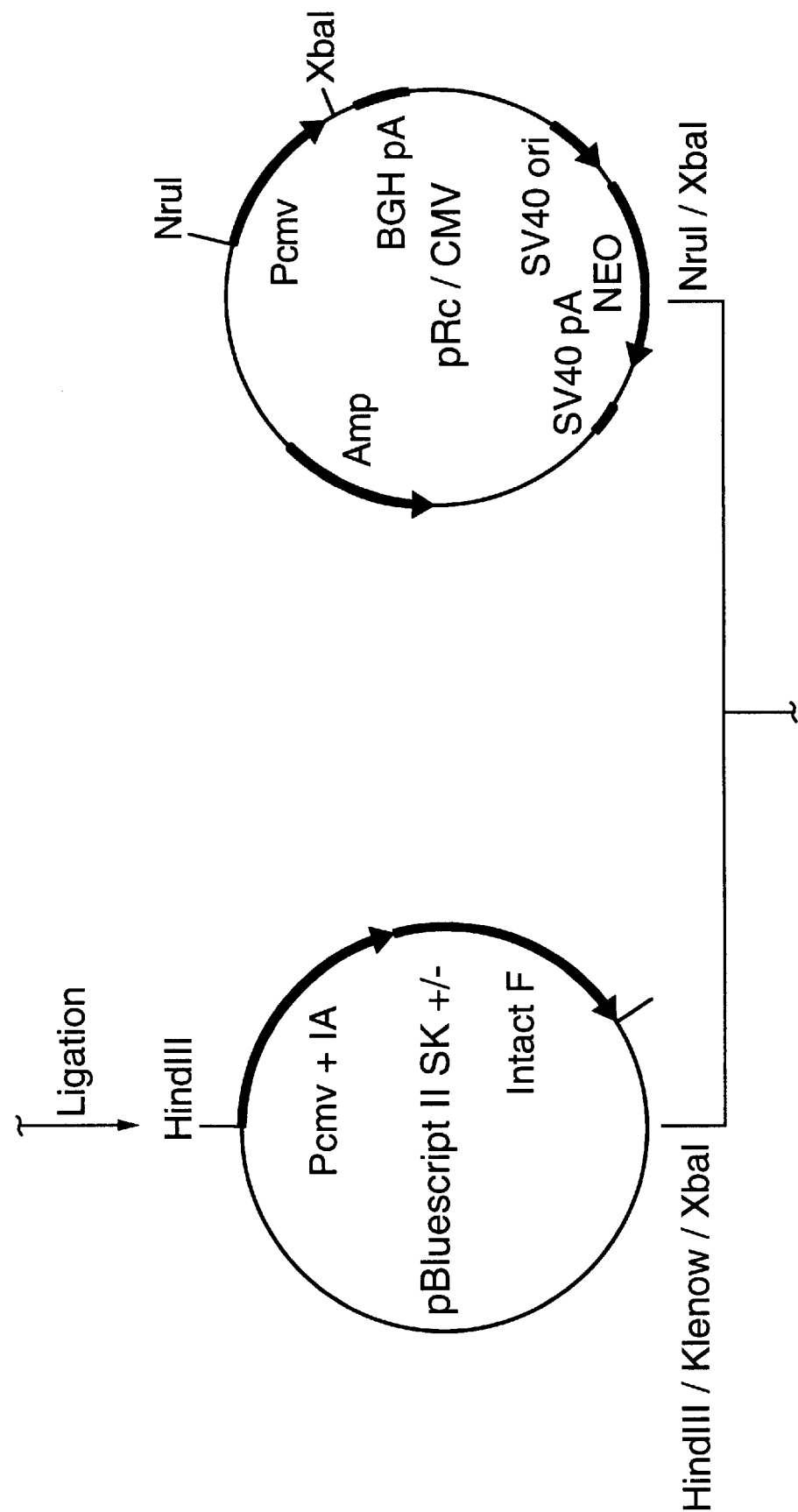
Figure 6D:
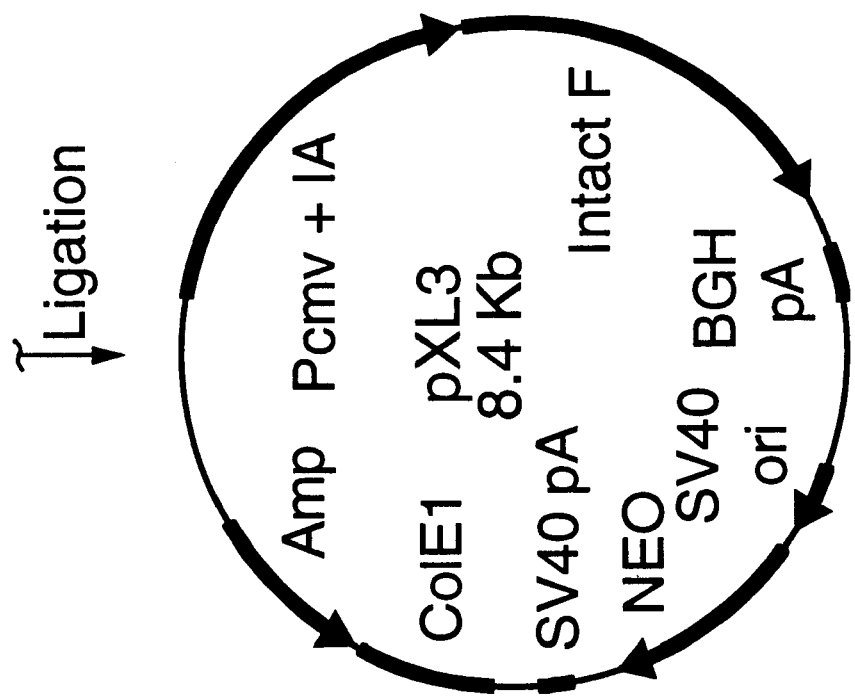

A set of four plasmid DNA constructs were made (as shown schematically in FIGS. 4 to 7) in which cDNA encoding the RSV-F was subcloned downstream of the immediate-early promoter, enhancer and intron A sequences of human cytomegalovirus (CMV) and upstream of the bovine growth hormone (BGH) poly-A site. The 1.6 Kb Sspl-PstI fragment containing the promoter, enhancer and intron A sequences of CMV Towne strain were initially derived from plasmid pRL43a obtained from Dr. G. S. Hayward of Johns Hopkins University (Pizzorno et al., J. Virol. 62, 1167–1179, 1988) and subcloned between EcoRV and Pstl sites of pBluescript 11 +/– (stratagene). For the construction of plasmids expressing the secretory form of the F protein (PXLI and pXL2 in FIGS. 4 and 5), the 1.6 Rb EcoRl-BamHl fragment containing the truncated form of the F cDNA originally cloned from a clinical isolate belonging to subgroup A was excised from pRSVF (ref. 18 and WO 93/14207) and subcloned between EcoRl and BamHl sites of pSG5 (Stratagene, ref. 14). Either the 1.6 Kb EcoRl-BamHl fragment or the 2.2 Xb Clal-BamHI fragment was then excised from the pSG5 construct, filled-in with Klenow and subcloned at the SmaI site of the pBluescript II SK +/– construct containing the promoter and intron A sequences. The 0.6 Kb ClaI-EcoRI fragment derived from pSG5 contained the intron II sequences from rabbit β-globin. Subsequently, the plasmids were digested with HindIII, filled-in with Klenow, and digested with XbaI to yield either a 3.2 or a 3.8 Kb fragment. These fragments were used to replaced the 0.8 Kb NruI-XbaI fragment containing the CMV promoter in pRc/CMV (Invitrogen), resulting in the final pXL1 and pXL2 constructs, respectively.

For the construction of plasmids expressing the full-length F protein (pXL3 and pXL4—FIGS. 6 and 7), the full length RSM F cDNA was excised as a 1.9 Xb EcoRl fragment from a recombinant pBluescript M13-SK (Stratagene) containing the insert (ref. 18 and WO 93/14207) and subcloned at the EcoRl site of pSG5 (Stratagene). Either the 1.9 Kb EcoRI fragment or the 2.5 Kb ClaI-BamHI fragment was then excised from the pSG5 construct, filled-in with Klenow and subcloned at the SmaI site of the pBluescript II SK +/– construct containing the promoter and intron A sequences. The rest of the construction for pXL3 and pXL4 was identical to that for pXL1 and pXL2, an described above. Therefore, except for the CMV promoter and intron A sequences, the rest of the vector components in pXL1 -4 were derived from plasmid pRc/CMV. Plasmids pXL1 and pXL2 were made to express a truncated/secretory form of the F protein which carried stop codons resulting in a C-terminal deletion of 4.8 amino acids including the transmembrane (TM) and the C-terminal cytosolic tail as compared to the intact molecule. In contrast, pXL3 and pXL4 were made to express the intact membrane-attached form of the RSV F molecule containing the TM and the cytosolic c-terminal tail. The rationale for the presence of the intron II sequences in pXL2 and pXL4 was that this intron was reported to mediate the correct splicing of RNAs. Since mRNA for the RSV-F has been suspected to have a tendency towards aberrant splicing, the presence of the intron II sequences might help to overcome this. All four plasmid constructs were confirmed by DNA sequencing analysis.

Plasmid DNA was purified using plasmid mega kits from Qiagen (Chatsworth, Calif., USA) according to the manufacturer's instructions.

EXAMPLE 2

This Example describes the immunization of mice. Mice are susceptible to infection by RSV as described in ref. 16.

Tibialis anterior muscles of groups of 9 BalB/c mice (male, 6–8 week old) (Jackson Lab.) were injected bilaterally with 2×50 $\mu$g (1 $\mu$g/$\mu$l in PBS) of the four plasmid constructs, respectively. Five days prior to the DNA injection, these muscles were treated bilaterally with cardiotoxin (2×50 $\mu$l of 10 $\mu$M in PBS, Latoxan, France). Pretreatment of the muscles with cardiotoxin has been reported to increase DNA uptake and to enhance the subsequent immune responses by the intramuscular route. These animals were boosted similarly a month later. The group of control mice was immunized with placebo according to the same schedule.

Sera were obtained periodically from immunized mice and analyzed for anti-RSV F-specific antibody titres by ELISA and for RSV-specific plaque-reduction titres in vitro. For the ELISA, 96-well plates were coated with purified RSV F protein at 50 ng/ml to which 2-fold serially diluted serum samples were applied. A goat-anti mouse antibody alkaline phosphatase conjugate was used. The assessment of the plaque reduction titres was essentially accordingly to the method of Prince et al. (ref. 19) using vaccine quanlity Vero cells. Four-fold serially diluted sera were incubated with 50 plaque forming units (pfu) of RSV, subtype A2 (Long strain), in culture medium at 37° C. for 1 hr in the presence of 5% $CO_2$. Vero cells were then infected with the mixture. Plaques ware fixed and developed 5 days later using mouse anti-RSV-F monoclonal antibodies and donkey anti-mouse antibodies conjugated to alkaline phosphatase. The RSV-specific plaque reduction titre was defined as the dilution of the serum sample yielding 60% reduction in the number of the plaques. This was derived by linear regression from correlating numbers of the remaining plaques with folds of the serial dilutions.

Seventy-five days after the boost immunization, mice were challenged intranasally with $10^{5.4}$ pfu (per animal) of mouse-adapted RMV, A2 subtype. Lungs were asceptically removed 4 days later, weighed and homogenized in 2 mL of complete culture medium. The number of pfu in the lung homogenate was determined as described by Prince et al (ref. 19) using vero cells.

The results of the immunizations are shown in Table 1 below, and were analysed using SigmaStat Software (Jandel Scientific Software).

Sera obtained from mice immunized with either construct pXL1, pXL2, pXL3 or pXL4 demonstrated significant anti-RSV F ELISA titres as compared to the placebo group (P<0.00061, Mann-Whitney Test). However, there is no significant difference among mice immunized with any of the constructs.

Sera obtained from mice immunized with constructs pXL1, pXL2, pXL3 or pXL4 demonstrated significant plaque reduction titres whereas sera obtained from the placebo group did not (P<0.0001, Mann-Whitney Test). However, there is no significant difference among mice immunized with any of the constructs.

The viral lung titres, four days after viral challenge, are also shown in Table 1. There is a significant difference between mice immunized with either construct pXL1, pXL2, pXL3 or pXL4 and the placebo group (P<0.0001, Mann-Whitney Test). In particular, no virus could be detected in the lungs of mice immunized with vector pXL2. The protection afforded by vector pXL3 was significantly lower than the other vectors.

In terms of the number of nice protected from RSV challenge, there is a significant difference between mice immunized with vectors pXL1, pXL2 and pXL4 and the placebo group or mice immunized with vector pXL3 (P<0.004, Fisher Exact Test). Furthermore, only the pXL2 vector which expresses the secretory form of the RSV F protein and contains the β-globin intron II was able to confer complete protection in all immunized mice. In contrast, the pXL3 vector which expresses the full length F protein and does not contain the intron II failed to induce significant protection. None of the mice in the placebo group were protected from viral challenge.

The data presented in Table 1 clearly demonstrate that immunization of a relevant RSV animal model with genes encoding F protein of RSV can protect against disease caused by this virus.

SUMMARY OF THE DISCLOSURE

In summary of this disclosure, the present invention provides certain novel vectors containing genes encoding an RSV F proteins, methods of immunization using such vectors and methods of diagnosis using such vectors. Modifications are possible within the scope of this invention.

TABLE 1

Protection of Mice Against RSV by Immunization with Genes Encoding the F Protein

| Immu- nogen | No. Mice | Anti-F Protein ELISA Titre ($Log_2$ ± SD)* | Mean Plaque Reduction Titre* ($Log_4$ ± SD) | Mean Virus Lung Titre@ (pfu/g lung) ($Log_{10}$ ± SD) | No. Fully Protected Mice** |
|---|---|---|---|---|---|
| pXL1 | 8 | 9.64 ± 1.85 | 3.74 ± 0.98 | 0.72 ± 0.99 | 5 |
| pXL2 | 9 | 12.42 ± 1.72 | 4.82 ± 0.51 | 0.00 ± 0.00 | 9 |
| pXL3 | 8 | 10.39 ± 2.05 | 4.59 ± 1.16 | 2.77 ± 0.72 | 0 |
| pXL4 | 9 | 12.08 ± 1.13 | 5.18 ± 0.43 | 0.66 ± 1.00 | 6 |
| Placebo*** | 12 | 6.12 ± 2.89 | 0.18 ± 0.62 | 3.92 ± 0.27 | 0 |

*Sera obtained 1 week prior to the viral challenge.
@Detection sensitivity of the assay was $10^{1.96}$ pfu/g lung.
**The term, fully protected mice, refers to animals with undetectable RSV titres in lungs (ref. 17)
***RSV F deficient pXL1

REFERENCES

1. McIntosh K., Canock, R. M. In: Fields B. N., Knipe, D. M., editors. Virology. New York: Raven Press: 1990: 1045–1072

2. Katz S. L., In: New Vaccine Development establishing priorities. Vol. 1. Washington: National Academic Press: 1985: 397–409.

3. Wert G. W., Sullender W. M., Biotechnology 1992; 20: 151–176

4. Johnson et al., J. Virol 1987, 61: 3163–3166

5. Pemberton et al., J. Gen Virol. 1987, 68: 2177–2182

6. Crowe, J. E., Vaccine 1995, 13; 415–421

7. WO 90/11092

8. WO 94/21797

9. Ulmer, Current Opinion, Invest Drugs, 1993, 2: 983–989.

10. Tang et al., Nature 1992, 356: 152–154

11. Furth et al. Analytical Biochemistry, 1992, 205: 365–368

12. Pizzorno et al., J. Virol. 1988, 62: 1167–1179

13. Chapman, B. S.; Thayer, R. N.; Vincent, K. A. and Haigwood, N. L., Nucl. Acids. Res. 1991, 19: 3979–3986.

14. Green, S. Isseman, I., and Sheer, E., Nucl. Acids. Res. 1988, 16: 369

15. Breathnack, R. and Harris, B. A., Nucl. Acids Res. 1983, 11: 7119–7136

16. Graham, B. S.; Perkins, M. D.; Wright, P. F. and Karzon, D. T. J. Mod. Virol. 1988 26: 153–162.

17. Nabel, G. J. 1993, Proc. Natl. Acad. Sci. USA 90: 11307–11311.

18. Du, R. P. et al. 1994., Biotechnology 12: 813–818.

19. Prince, G. A. et al, 1978. Ame. J. Patho. 93: 771–790.

What we claim is:

1. An immunogenic composition for in vivo administration to a host for the generation in the host of protective antibodies to RSV F protein, comprising a plasmid vector comprising:
   a first nucleotide sequence encoding a RSV F protein or a RSV F protein fragment that generates antibodies that specifically react with RSV F protein;
   a promoter sequence operatively coupled to said first nucleotide sequence for expression of said RSV F protein in the host, and
   a second nucleotide sequence located between said first nucleotide sequence and said promoter sequence and comprising a pair of splice sites to prevent aberrant mRNA splicing and to increase expression of said RSV F protein in vivo from said vector in the host, and a pharmaceutically acceptable carrier.

2. The composition of claim 1 wherein said first nucleotide sequence encodes a full-length RSV F protein.

3. The composition of claim 1 wherein said first nucleotide sequence encodes a RSV F protein from which the transmembrane region is absent.

4. The composition of claim 1 wherein said first nucleotide sequence encodes a RSV F protein and contains a translational stop codon immediately upstream of the start of the transmembrane coding region to prevent translation of the transmembrane coding region.

5. The composition of claim 1 wherein said promoter sequence is a immediate early cytomegalovirus promoter.

6. The composition of claim 1 wherein said second nucleotide sequence is that of rabbit β-globin intron II.

7. The composition of claim 1 wherein the plasmid vector is pXL2 as shown in FIG. 5.

8. The composition of claim 1 wherein the plasmid vector is pXL4 as shown in FIG. 7.

9. The composition of claim 1 wherein the plasmid vector is pXL1 as shown in FIG. 4.

10. The composition of claim 1 wherein the plasmid vector is pXL3 as shown in FIG. 6.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1886 base pairs
      (B) TYPE: nucleic acid
      (C) STRANDEDNESS: single
      (D) TOPOLOGY: linear (xi) SEQUENCE DESCRIPTION: SEQ ID NO:1:

```
ATGGAGTTGC CAATCCTCAA AGCAAATGCA ATTACCACAA TCCTCGCTGC AGTCACATTT      60

TGCTTTGCTT CTAGTCAAAA CATCACTGAA GAATTTTATC AATCAACATG CAGTGCAGTT     120

AGCAAAGGCT ATCTTAGTGC TCTAAGAACT GGTTGGTATA CTAGTGTTAT AACTATAGAA     180

TTAAGTAATA TCAAGGAAAA TAAGTGTAAT GGAACAGATG CTAAGGTAAA ATTGATGAAA     240

CAAGAATTAG ATAAATATAA AAATGCTGTA ACAGAATTGC AGTTGCTCAT GCAAAGCACA     300

CCAGCAGCAA ACAATCGAGC CAGAAGAGAA CTACCAAGGT TTATGAATTA TACACTCAAC     360

AATACCAAAA AAACCAATGT AACATTAAGC AAGAAAAGGA AAAGAAGATT TCTTGGTTTT     420

TTGTTAGGTG TTGGATCTGC AATCGCCAGT GGCATTGCTG TATCTAAGGT CCTGCACTTA     480

GAAGGAGAAG TGAACAAGAT CAAAAGTGCT CTACTATCCA CAAACAAGGC CGTAGTCAGC     540

TTATCAAATG GAGTTAGTGT CTTAACCAGC AAAGTGTTAG ACCTCAAAAA CTATATAGAT     600

AAACAATTGT TACCTATTGT GAATAAGCAA AGCTGCAGAA TATCAAATAT AGAAACTGTG     660

ATAGAGTTCC AACAAAAGAA CAACAGACTA CTAGAGATTA CCAGGGAATT TAGTGTTAAT     720

GCAGGTGTAA CTACACCTGT AAGCACTTAC ATGTTAACTA ATAGTGAATT ATTGTCATTA     780

ATCAATGATA TGCCTATAAC AAATGATCAG AAAAAGTTAA TGTCCAACAA TGTTCAAATA     840

GTTAGACAGC AAAGTTACTC TATCATGTCC ATAATAAAAG AGGAAGTCTT AGCATATGTA     900

GTACAATTAC CACTATATGG TGTGATAGAT ACACCTTGTT GGAAATTACA CACATCCCCT     960

CTATGTACAA CCAACACAAA AGAAGGGTCA AACATCTGTT TAACAAGAAC TGACAGAGGA    1020

TGGTACTGTG ACAATGCAGG ATCAGTATCT TTCTTCCCAC AAGCTGAAAC ATGTAAAGTT    1080

CAATCGAATC GAGTATTTTG TGACACAATG AACAGTTTAA CATTACCAAG TGAAGTAAAT    1140

CTCTGCAATG TTGACATATT CAATCCCAAA TATGATTGTA AAATTATGAC TTCAAAAACA    1200

GATGTAAGCA GCTCCGTTAT CACATCTCTA GGAGCCATTG TGTCATGCTA TGGCAAAACT    1260

AAATGTACAG CATCCAATAA AAATCGTGGA ATCATAAAGA CATTTTCTAA CGGGTGTGAT    1320

TATGTATCAA ATAAAGGGGT GGACACTGTG TCTGTAGGTA ACACATTATA TTATGTAAAT    1380

AAGCAAGAAG GCAAAAGTCT CTATGTAAAA GGTGAACCAA TAATAAATTT CTATGACCCA    1440

TTAGTATTCC CCTCTGATGA ATTTGATGCA TCAATATCTC AAGTCAATGA GAAGATTAAC    1500

CAGAGTTTAG CATTTATTCG TAAATCCGAT GAATTATTAC ATAATGTAAA TGCTGGTAAA    1560

TCAACCACAA ATATCATGAT AACTACTATA ATTATAGTGA TTATAGTAAT ATTGTTATCA    1620

TTAATTGCTG TTGGACTGCT CCTATACTGT AAGGCCAGAA GCACACCAGT CACACTAAGC    1680

AAGGATCAAC TGAGTGGTAT AAATAATATT GCATTTAGTA ACTGAATAAA AATAGCACCT    1740

AATCATGTTC TTACAATGGT TTACTATCTG CTCATAGACA ACCATCTAT CATTGGATTT    1800

TCTTAAAATC TGAACTTCAT CGAAACTCTT ATCTATAAAC CATCTCACTT ACACTATTTA    1860
```

AGTAGATTCC TAGTTTATAG TTATAT                                                                     1886

(2) INFORMATION FOR SEQ ID NO:2:

(i) SEQUENCE CHARACTERISTICS:
        (A) LENGTH: 594 amino acids
        (B) TYPE: amino acid
        (C) STRANDEDNESS: single
        (D) TOPOLOGY: linear (xi) SEQUENCE DESCRIPTION: SEQ ID NO:2:

```
Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Arg Ala Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Arg Ser Cys Arg Ile Ser Asn Ile Glu Thr Val Ile Glu Phe Gln
    210                 215                 220

His Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asn Ala Gly Ser Val Ser Phe Phe
            340                 345                 350

Pro Gln Ala Glu Thr Cys Lys Val Gln Ser Asn Arg Val Phe Cys Asp
```

```
                355                 360                 365
Thr Met Asn Ser Leu Thr Leu Pro Ser Glu Val Asn Leu Cys Asn Val
        370                 375                 380
Asp Ile Phe Asn Pro Lys Tyr Asp Cys Lys Ile Met Thr Ser Lys Thr
385                 390                 395                 400
Asp Val Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
                435                 440                 445
Thr Val Ser Val Gly Asn Thr Leu Tyr Tyr Val Asn Lys Gln Glu Gly
                450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Leu Val Phe Pro Ser Asp Glu Phe Asp Ala Ser Ile
                500                 505                 510
Ser Gln Val Asn Glu Lys Ile Asn Gln Ser Leu Ala Phe Ile Arg Lys
                515                 520                 525
Ser Asp Glu Leu Leu His Asn Val Asn Ala Gly Lys Ser Thr Thr Asn
                530                 535                 540
Ile Met Ile Thr Thr Ile Ile Glu Ile Ile Val Ile Leu Leu Ser
545                 550                 555                 560
Leu Ile Ala Val Gly Leu Leu Leu Tyr Cys Lys Ala Arg Ser Thr Pro
                565                 570                 575
Val Thr Leu Ser Lys Asp Gln Leu Ser Gly Ile Asn Asn Ile Ala Phe
                580                 585                 590
Ser Asn (2) INFORMATION FOR SEQ ID NO:3:

(i) SEQUENCE CHARACTERISTICS:
        (A) LENGTH: 1904 base pairs
        (B) TYPE: nucleic acid
        (C) STRANDEDNESS: single
        (D) TOPOLOGY: linear (xi) SEQUENCE DESCRIPTION: SEQ ID NO:3:

ATGGAGTTGC CAATCCTCAA AGCAAATGCA ATTACCACAA TCCTCGCTGC AGTCACATTT      60

TGCTTTGCTT CTAGTCAAAA CATCACTGAA GAATTTTATC AATCAACATG CAGTGCAGTT    120

AGCAAAGGCT ATCTTAGTGC TCTAAGAACT GGTTGGTATA CTAGTGTTAT AACTATAGAA    180

TTAAGTAATA TCAAGGAAAA TAAGTGTAAT GGAACAGATG CTAAGGTAAA ATTGATGAAA    240

CAAGAATTAG ATAAATATAA AAATGCTGTA ACAGAATTGC AGTTGCTCAT GCAAAGCACA    300

CCAGCAGCAA ACAATCGAGC CAGAAGAGAA CTACCAAGGT TTATGAATTA TACACTCAAC    360

AATACCAAAA AAACCAATGT AACATTAAGC AAGAAAAGGA AAGAAGATT TCTTGGTTTT     420

TTGTTAGGTG TTGGATCTGC AATCGCCAGT GGCATTGCTG TATCTAAGGT CCTGCACTTA    480

GAAGGAGAAG TGAACAAGAT CAAAAGTGCT CTACTATCCA CAAACAAGGC CGTAGTCAGC    540

TTATCAAATG GAGTTAGTGT CTTAACCAGC AAAGTGTTAG ACCTCAAAAA CTATATAGAT    600

AAACAATTGT TACCTATTGT GAATAAGCAA AGCTGCAGAA TATCAAATAT AGAAACTGTG    660

ATAGAGTTCC AACAAAAGAA CAACAGACTA CTAGAGATTA CCAGGGAATT TAGTGTTAAT    720
```

```
GCAGGTGTAA CTACACCTGT AAGCACTTAC ATGTTAACTA ATAGTGAATT ATTGTCATTA    780

ATCAATGATA TGCCTATAAC AAATGATCAG AAAAAGTTAA TGTCCAACAA TGTTCAAATA    840

GTTAGACAGC AAAGTTACTC TATCATGTCC ATAATAAAAG AGGAAGTCTT AGCATATGTA    900

GTACAATTAC CACTATATGG TGTGATAGAT ACACCTTGTT GGAAATTACA CACATCCCCT    960

CTATGTACAA CCAACACAAA AGAAGGGTCA AACATCTGTT TAACAAGAAC TGACAGAGGA   1020

TGGTACTGTG ACAATGCAGG ATCAGTATCT TTCTTCCCAC AAGCTGAAAC ATGTAAAGTT   1080

CAATCGAATC GAGTATTTTG TGACACAATG AACAGTTTAA CATTACCAAG TGAAGTAAAT   1140

CTCTGCAATG TTGACATATT CAATCCCAAA TATGATTGTA AAATTATGAC TTCAAAAACA   1200

GATGTAAGCA GCTCCGTTAT CACATCTCTA GGAGCCATTG TGTCATGCTA TGGCAAAACT   1260

AAATGTACAG CATCCAATAA AAATCGTGGA ATCATAAAGA CATTTTCTAA CGGGTGTGAT   1320

TATGTATCAA ATAAAGGGGT GGACACTGTG TCTGTAGGTA ACACATTATA TTATGTAAAT   1380

AAGCAAGAAG GCAAAAGTCT CTATGTAAAA GGTGAACCAA TAATAAATTT CTATGACCCA   1440

TTAGTATTCC CCTCTGATGA ATTTGATGCA TCAATATCTC AAGTCAATGA GAAGATTAAC   1500

CAGAGTTTAG CATTTATTCG TAAATCCGAT GAATTATTAC ATAATGTAAA TGCTGGTAAA   1560

TCAACCACAA ATATCATGAC TTGATAATGA GGATCCATAA CTACTATAAT TATAGTGATT   1620

ATAGTAATAT TGTTATCATT AATTGCTGTT GGACTGCTCC TATACTGTAA GGCCAGAAGC   1680

ACACCAGTCA CACTAAGCAA GGATCAACTG AGTGGTATAA ATAATATTGC ATTTAGTAAC   1740

TGAATAAAAA TAGCACCTAA TCATGTTCTT ACAATGGTTT ACTATCTGCT CATAGACAAC   1800

CCATCTATCA TTGGATTTTC TTAAAATCTG AACTTCATCG AAACTCTTAT CTATAAACCA   1860

TCTCACTTAC ACTATTTAAG TAGATTCCTA GTTTATAGTT ATAT                    1904

(2) INFORMATION FOR SEQ ID NO:4:

(i) SEQUENCE CHARACTERISTICS:
        (A) LENGTH: 527 amino acids
        (B) TYPE: amino acid
        (C) STRANDEDNESS: single
        (D) TOPOLOGY: linear (xi) SEQUENCE DESCRIPTION: SEQ ID NO:4:

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Met Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
```

```
                 145                   150                   155                   160
Glu Gly Glu Val Asn Lys Ile Lys Ser Ala Leu Leu Ser Thr Asn Lys
                    165                   170                   175

Ala Val Val Ser Leu Ser Asn Gly Val Ser Val Leu Thr Ser Lys Val
                    180                   185                   190

Leu Asp Leu Lys Asn Tyr Ile Asp Lys Gln Leu Leu Pro Ile Val Asn
                    195                   200                   205

Lys Gln Ser Cys Arg Ile Ser Asn Ile Glu Thr Val Ile Glu Phe Gln
                    210                   215                   220

His Lys Asn Asn Arg Leu Leu Glu Ile Thr Arg Glu Phe Ser Val Asn
225                     230                   235                   240

Ala Gly Val Thr Thr Pro Val Ser Thr Tyr Met Leu Thr Asn Ser Glu
                    245                   250                   255

Leu Leu Ser Leu Ile Asn Asp Met Pro Ile Thr Asn Asp Gln Lys Lys
                    260                   265                   270

Leu Met Ser Asn Asn Val Gln Ile Val Arg Gln Gln Ser Tyr Ser Ile
                    275                   280                   285

Met Ser Ile Ile Lys Glu Glu Val Leu Ala Tyr Val Val Gln Leu Pro
290                     295                   300

Leu Tyr Gly Val Ile Asp Thr Pro Cys Trp Lys Leu His Thr Ser Pro
305                     310                   315                   320

Leu Cys Thr Thr Asn Thr Lys Glu Gly Ser Asn Ile Cys Leu Thr Arg
                    325                   330                   335

Thr Asp Arg Gly Trp Tyr Cys Asp Asn Ala Gly Ser Val Ser Phe Phe
                    340                   345                   350

Pro Gln Ala Glu Thr Cys Lys Val Gln Ser Asn Arg Val Phe Cys Asp
                    355                   360                   365

Thr Met Asn Ser Leu Thr Leu Pro Ser Glu Val Asn Leu Cys Asn Val
                    370                   375                   380

Asp Ile Phe Asn Pro Lys Tyr Asp Cys Lys Ile Met Thr Ser Lys Thr
385                     390                   395                   400

Asp Val Ser Ser Ser Val Ile Thr Ser Leu Gly Ala Ile Val Ser Cys
                    405                   410                   415

Tyr Gly Lys Thr Lys Cys Thr Ala Ser Asn Lys Asn Arg Gly Ile Ile
                    420                   425                   430

Lys Thr Phe Ser Asn Gly Cys Asp Tyr Val Ser Asn Lys Gly Val Asp
                    435                   440                   445

Thr Val Ser Val Gly Asn Thr Leu Tyr Tyr Val Asn Lys Gln Glu Gly
                    450                   455                   460

Lys Ser Leu Tyr Val Lys Gly Glu Pro Ile Ile Asn Phe Tyr Asp Pro
465                     470                   475                   480

Leu Val Phe Pro Ser Asp Glu Phe Asp Ala Ser Ile Ser Gln Val Asn
                    485                   490                   495

Glu Lys Ile Asn Gln Ser Leu Ala Phe Ile Arg Lys Ser Asp Glu Leu
                    500                   505                   510

Leu His Asn Val Asn Ala Gly Lys Ser Thr Thr Asn Ile Met Thr
                    515                   520                   525

(2) INFORMATION FOR SEQ ID NO:5:

(i) SEQUENCE CHARACTERISTICS:
        (A) LENGTH: 573 base pairs
        (B) TYPE: nucleic acid
        (C) STRANDEDNESS: single
        (D) TOPOLOGY: linear
```

-continued (xi) SEQUENCE DESCRIPTION: SEQ ID NO:5:

```
GTGAGTTTGG GGACCCTTGA TTGTTCTTTC TTTTTCGCTA TTGTAAAATT CATGTTATAT      60

GGAGGGGGCA AAGTTTTCAG GGTGTTGTTT AGAATGGGAA GATGTCCCTT GTATCACCAT     120

GGACCCTCAT GATAATTTTG TTTCTTTCAC TTTCTACTCT GTTGACAACC ATTGTCTCCT     180

CTTATTTTCT TTTCATTTTC TGTAACTTTT TCGTTAAACT TTAGCTTGCA TTTGTAACGA     240

ATTTTTAAAT TCACTTTTGT TTATTTGTCA GATTGTAAGT ACTTTCTCTA ATCACTTTTT     300

TTTCAAGGCA ATCAGGGTAT ATTATATTGT ACTTCAGCAC AGTTTTAGAG AACAATTGTT     360

ATAATTAAAT GATAAGGTAG AATATTTCTG CATATAAATT CTGGCTGGCG TGGAAATATT     420

CTTATTGGTA GAAACAACTA CATCCTGGTC ATCATCCTGC CTTTCTCTTT ATGGTTACAA     480

TGATATACAC TGTTTGAGAT GAGGATAAAA TACTCTGAGT CCAAACCGGG CCCCTCTGCT     540

AACCATGTTC ATGCCTTCTT CTTTTTCCTA CAG                                  573
```